US011406671B2

(12) United States Patent
Liu et al.

(10) Patent No.: US 11,406,671 B2
(45) Date of Patent: Aug. 9, 2022

(54) COMPOSITIONS AND METHODS FOR AUGMENTING THE NASAL MICROBIOME

(71) Applicants: THE TRANSLATIONAL GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US)

(72) Inventors: Cindy Liu, Flagstaff, AZ (US); Lance B. Price, Flagstaff, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 15/568,793

(22) PCT Filed: Apr. 25, 2016

(86) PCT No.: PCT/US2016/029171
§ 371 (c)(1),
(2) Date: Oct. 23, 2017

(87) PCT Pub. No.: WO2016/172686
PCT Pub. Date: Oct. 27, 2016

(65) Prior Publication Data
US 2018/0185420 A1 Jul. 5, 2018

Related U.S. Application Data

(60) Provisional application No. 62/152,547, filed on Apr. 24, 2015.

(51) Int. Cl.
*A61K 35/741* (2015.01)
*A61K 9/00* (2006.01)
*A61K 31/351* (2006.01)

(52) U.S. Cl.
CPC .......... *A61K 35/741* (2013.01); *A61K 9/0043* (2013.01); *A61K 31/351* (2013.01)

(58) Field of Classification Search
None
See application file for complete search history.

(56) References Cited

U.S. PATENT DOCUMENTS

| 2010/0074872 | A1* | 3/2010 | Blaser | A61K 35/74 |
| | | | | 424/93.4 |
| 2011/0256179 | A1 | 10/2011 | Roos et al. | |
| 2011/0311588 | A1 | 12/2011 | Comans | |
| 2012/0225098 | A1 | 9/2012 | Kaplan et al. | |
| 2013/0121968 | A1* | 5/2013 | Quay | G06F 19/34 |
| | | | | 424/93.4 |

FOREIGN PATENT DOCUMENTS

WO    WO-2013155370 A1 * 10/2013 .......... A61K 35/744

OTHER PUBLICATIONS

Forsyth. My Mouth, My Nose, My Microbes Update!.Lemon Lab. Datasheet [online]. The Forsyth Institute. [retrieved on May 8, 2019]. Copyright 2014.The Forsyth Institute. Retrieved from the internet: pp. 1-6. specif. pp. 1, 6.*
Saranraj, P. et al. 2013. Lactic acid bacteria and its antimicrobial properties: a review. International Journal of Pharmaceutical & Biological Archives 4(6): 1124-1133. specif. pp. 1124, 1125, 1126, 1127, 1128.*
Gluck, U. et al. 2003. Ingested probiotics reduce nasal colonization with pathogenic bacteria (*Staphylococcus aureus, Streptococcus pneumoniae*, and B-hemolytic streptococci). American Journal of Clinical Nutrition 77: 517-520. specif. pp. 517, 518, 520.*
Prinsulaka, O. et al. Jan. 2015. In vitro screening of lactic acid bacteria for multi-strain probiotics. Livestock Science 174: 66-73. specif. p. 66.*
Laufer, A.S. et al. 2011. Microbial communities of the upper respiratory tract and otitis media in children. mBio 2(1): 1-6. specif. pp. 1, 4.*
Axelsson, L. Lactic acid bacteria: classification and physiology. In: Lactic Acid Bacteria, Microbiological and Functional Aspects. Eds. Salminen, von Wright and Ouwehand. Copyright 2004 Marcel Dekker, Inc. pp. 1-67. specif. pp. 1, 5, 14, 17.*
Gluck, U. et al. 2003. Ingested probiotics reduce nasal colonization with pathogenic bacteria (*Staphylococcus aureus, Streptococcus pneumoniae*, and B-hemolytic streptococci. American Journal of Clinical Nutrition 77: 517-520. specif. pp. 517, 518, 519, 520.*
Kluytmans, J. 1998. Reduction of surgical site infections in major surgery by elimination of nasal carriage of *Staphylococcus aureus*. Journal of Hospital Infection 40: S25-S29. specif. pp. S25, S27, S28.*
Biesbroek, G. et al. 2014. The impact of breastfeeding on nasopharyngeal microbial communities in infants. American Journal of Respiratory Critical Care Medicine 190(3): 298-308. specif. pp. 298, 299, 300, 301, 302.*
Frank, D.N. et al. 2010. The human nasal microbiota and *Staphylococcus aureus* carriage. PLoS ONE 5(5): 1-15. specif, pp. 1, 2, 3, 4, 8, 9, 12.*
Belkum et al., Reclassification of *Staphylococcus aureus* nasal carriage types. The J Infect Dis 199, 1820-1826 (2009).
Andersen et al., Influence of host genetics and environment on nasal carriage of *Staphylococcus aureus* in danish middle-aged and elderly twins. J Infect Dis 206, 1178-1184 (2012).
Li et al., Symbiotic gut microbes modulate human metabolic phenotypes. Proc Natl Acad Sci U S A 105, 2117-2122 (2008).
Peterson et al., The NIH Human Microbiome Project. Genome Res 19, 2317-2323 (2009).

(Continued)

Primary Examiner — Olivia M. Wise
Assistant Examiner — Sharon M. Papciak
(74) Attorney, Agent, or Firm — Rodney J. Fuller; Booth Udall Fuller, PLC

(57) ABSTRACT

Embodiments of the invention provide a method of reducing colonization of a subject's anterior nares and/or nasal cavity by a microorganism (e.g., *Staphylococcus aureus*). In some aspects, the method may include administering a pharmaceutical composition to the subject, wherein the pharmaceutical composition comprises a therapeutically effective amount of at least one probiotic.

20 Claims, 10 Drawing Sheets

Specification includes a Sequence Listing.

(56) References Cited

OTHER PUBLICATIONS

Grice et al., Topographical and temporal diversity of the human skin microbiome. Science 324, 1190-1192 (2009).

Lemon et al., Comparative analyses of the bacterial microbiota of the human nostril and oropharynx. mBio 1, (2010).

Frank et al., The human nasal microbiota and *Staphylococcus aureus* carriage. PLoS One 5, e10598 (2010).

Uehara et al., Bacterial interference among nasal inhabitants: eradication of *Staphylococcus aureus* from nasal cavities by artificial implantation of Corynebacterium sp. J Hosp Infect 44, 127-133 (2000).

Yan et al., Nasal microenvironments and interspecific interactions influence nasal microbiota complexity and *S. aureus* carriage. Cell Host Microbe 14, 631-640 (2013).

Camarinha-Silva et al, The temporal dynamics of bacterial communities across human anterior nares. Environ Microbiol Rep 4, 126-132 (2012).

Liu et al., BactQuant: an enhanced broad-coverage bacterial quantitative real-time PCR assay. BMC microbiology 12, 56 (2012).

Liu et al., Male circumcision significantly reduces prevalence and load of genital anaerobic bacteria. mBio 4, e00076 (2013).

Wertheim et al., The role of nasal carriage in *Staphylococcus aureu* infections. Lancet Infect Dis 5, 751-762 (2005).

Munckhof et al., Nasal carriage of *Staphylococcus aureu*, including community-associated methicillin-resistant strains, in Queensland adults. Clin Microbiol Infect 15, 149-155 (2009).

Olsen et al., *Staphylococcus aureus* nasal carriage is associated with serum 25-hydroxyvitamin D levels, gender and smoking status. The Tromso Staph and Skin Study. Eur J Clin Microbiol Infect Dis 31, 465-473 (2012).

Gause, G. F., The struggle for existence. The Williams & Wilkins Company, Baltimore (1934).

Fierer et al., From Animalcules to an Ecosystem: Application of Ecological Concepts to the Human Microbiome. Annu Rev Ecol Evol Syst 43, 137-155 (2012).

Pettigrew et al., Upper respiratory tract microbial communities, acute otitis media pathogens, and antibiotic use in healthy and sick children. Appl Environ Microbiol 78(17), 6262-6270 (2012).

Liu, C. M., et al. Medical therapy reduces microbiota diversity and evenness in surgically recalcitrant chronic rhinosinusitis. Int. Forum Allergy Rhinol. 2013; 3(10):775-781.

Ravel, J., et al. Vaginal microbiome of reproductive-age women. Proc. Natl. Acad. Sci. U.S.A. 2011; 108(Suppl. 1):4680-4687.

Wolak, M. E., et al. Guidelines for estimating repeatability. Methods Ecol. Evol. 2012; 3(1):129-137.

Edgar, R. C., et al. UCHIME improves sensitivity and speed of chimera detection. Bioinformatics 2011; 27(16):2194-2200.

Caporaso, J. G., et al. QIIME allows analysis of high-throughput community sequencing data. Nat. Methods 2010. 7(5):335-336.

Cole, J. R., et al. The Ribosomal Database Project: Improved alignments and new tools for rRNA analysis. Nucleic Acids Res. 2009; 37(Database issue):D141-D145.

McDonald, D., et al. An improved Greengenes taxonomy with explicit ranks for ecological and evolutionary analyses of bacteria and archaea. Isme J. 2012; 6(3):610-618.

Gajer, P., et al. Temporal dynamics of the human vaginal microbiota. Sci. Transl. Med. 2012; 4(132):132ra152.

Schieke, T. H., et al. Estimating heritability for cause specific mortality based on twin studies. Lifetime Data Anal. 2014; 20(2):210-233.

Von Eiff, C., et al. Nasal carriage as a source of *Staphylococcus aureus* bacteremia. N Engl J Med 2001; 344(1):11-16.

Wertheim, H. F. L., et al. Risk and outcome of nosocomial *Staphylococcus aureus* bacteraemia in nasal carriers versus non-carriers. The Lancet 2004; 364(9435):703-705.

Stevens, A. M., et al. Methicillin-Resistant *Staphylococcus aureus* carriage and risk factors for skin infections, Southwestern Alaska, USA. Emerging Infectious Disease 2010; 16(5):797-803.

Farley, J. E., et al. Prevalence, risk factors, and molecular epidemiology of methicillin-resistant *Staphylococcus aureus* among newly arrested mend in Baltimore, Maryland. American Journal of Infection Control 2008; 36(9):644-650.

Ellis, M. W., et al. Presence and molecular epidemiology of virulence factors in methicillin-resistant *Staphylococcus aureus* strains colonizing and infecting soldiers. Journal of Clinical Microbiology 2009; 47(4):940-945.

Lamaro-Cardoso, J., et al. Molecular epidemiology and risk factors for nasal carriage of *Staphylococcus aureus* and methicillin-resistant *S. aureus* in infants attending day care centers in Brazil. Journal of Clinical Microbiology 2009; 47(12):3991-3997.

Patel, J. B., et al. Mupirocin resistance. Clin Infect Dis 2009; 49(6):935-941.

Wertheim, H. F., et al. Mupirocin prophylaxis against nosocomial *Staphylococcus aureus* infections in nonsurgical patients: a randomized study. Annals of Internal Medicine 2004; 140(6):419-425.

Cadilla, A., et al. Association of high-level mupirocin resistance and multidrug-resistant methicillin-resistant *Staphylococcus aureus* at an academic center in the Midwestern United States. Journal of Clincal Microbiology 2011; 49(1):95-100.

Ammerlaan, H. S., et al. Eradication of carriage with methicillin-resistant *Staphylococcus aureus*: determinants of treatment failure. J Antimicrob Chemother 2011; 66(10):2418-2424.

Coates, T., et al. Nasal decolonization of *Staphyloccccus aureus* with mupirocin: strengths, weakness and future prospects. J Antimicrob Chemother 2009; 64(1):9-15.

Gorwitz, R. J., et al. Changes in the prevelance of nasal colonization with *Staphylococcus aureus* in the United States 2001-2004. The Journal of Infectious Diseases 2008; 197(9):1226-1234.

Krismer, B., et al. Nutrient limitation governs *Staphylococcus aureus* metabolism and nich adaptation in the human nose. PLoS Pathogens 2014; 10(1):e1003862.

Xia, G., et al. Glycosylation of wall teichoic acid in *Staphylococcus aureus* by TArM. The Journal of Biological Chemistry 2010; 285(18):13405-13415.

Weidenmaier, C., et al. Role of teichoic acids in *Staphylococcus aureus* nasal colonization, a major risk factor in nosocomial infections. Nature Medicine 2004; 10(3):243-245.

Ernst, C. M., et al. The bacterial defensing resistance protein MprF consists of separable domains for lipid ysinylation and antimicrobial peptide repulsion PLoS Pathogens 2009; 58(11):e1000660.

Kuehnert, M. J., et al. Prevalence of *Staphylococcus aureus* nasal colonization in the United States 2001-2002. The Journal of Infectious Diseases 2006; 193(2):172-179.

Ruimy, R., et al. Comparisons between geographically diverse samples of carried *Staphylococcus aureus*. Journal of Bacteriology 2009; 191(18):5577-5583.

Burian, M., et al. Temporal expression of adhesion factors and activity of global regulators during establishment of *Staphylococcus aureus* nasal colonization. The Journal of Infectious Diseases 2010; 201(9):1414-1421.

Burian, M., et al. Regulatory adaption of *Staphylococcus aureus* during nasal colonization of humans. PLoS One 2010; 5(4):e10040.

Corrigan, R. M., et al. Surface proteins that promote adherence of *Staphylococcus aureus* to human desqamated nasal epithelial cells. BMC microbiology 2009; 9:22.

Wertheim, H. F., et al. Key role for clumping factor B in *Staphylococcus aureus* nasal colonization of humans. PLoS Medicine 2008; 5(1):e17.

Wertheim, H. F., et al. Nose picking and nasal carriage of *Staphylococcus aureus*. Infection Control and Hospital Epidemiology 2006; 27(8):863-867.

Olsen, K., et al. Prevalence and population structure of *Staphylococcus aureus* nasal carriage in healthcare workers in a general population, the Tromso Staph and Skin Study. Epidemiology and Infection 2013; 141(1):143-152.

Fadrosh, D. W., et al. An improved dual-indexing approach for multiplexed 16S rRNA gene sequencing on the Illumina MiSeq platform. Microbiome 2014; 2(1):6.

Ammerlaan, H. S., et al. Eradication of methicillin-resistant *Staphylococcus aureus* carriage: a systematic review. Clin Infect Dis 2009; 48(7):922-930.

Bocher, S., et al. The search and destroy strategy prevents spread and long-term carriage of methicillin-resistant *Staphyococcus aureus*:

(56) References Cited

OTHER PUBLICATIONS results from the follow-up screening of a large ST22 (E-MRASA 15) outbreak in Denmark. Clinical Microbiology and Infection 2010; 16(9):1427-1434.
Lee, H., et al. Coexistence of mupirocin and antiseptic resistance in methicillin-resistant *Staphylococcus aureus* isolates from Korea. Diagnostic Microbiology and Infectious Disease 2013; 75(3):308-312.
Miller, L. G., et al. Prospective investigation of nasal mupirocin hexachlorophene body wash, and systemic antibiotics for prevention of recurrent community-associated methicillin-resistant *Staphylococcus aureus* infections. Antimicrobial Agents and Chemotherapy 2012; 56(2):1084-1086.
Lu, S. Y., et al. Methicillin-resistant *Staphylococcus aureus* nasal colonization among adult patients visiting emergency department in a medical center in Taiwan. PLoS One 2011; 6(6):e18620.
Miller, L. G., et al. *Staphylococcus aureus* colonization among household contacts of patients with skin infections: risk factors, strain discordance, and complex ecology. Clin Infect Dis 2012; 54(11):1523-1535.
Fritz, S. A., et al. Mupirocin and chlorhexidine resistance in *Staphylococcus aureus* in patients with community onset skin and soft tissue infections. Antimicrobial Agents and Chemotherapy 2013; 57(1):559-568.
McDaniel, J. S., et al. Chlorhexidine and Mupirocin susceptibilities of methicillin-resistant *Staphylococcus aureus* from colonized nursing home residents. Antimicrobial Agents and Chemotherapy 2013; 57(1):552-558.
Bode, L. G., et al. preventing surgical-site infections in nasal carriers of *Staphylococcus aureus*. N Engl J Med 2010; 362(1):9-17.
Huskins, W. C., et al. Intervention to reduce transmission of resistant bacteria in intensive care. N Engl J Med 2011; 364(15):1407-1418.
Kim, D. H., et al. Institutional prescreening for detection and eradication of methicillin-resistant *tphayococcus aureus* in patients undergoing elective orthopeaedic surgery. The Journal of Bone and Joint Surgery 2010; 92(9):1820-1826.
Pofahl, W. E., et al. Active surveillance screening of MRSA and eradication of the carrier state decreases surgical-site infections caused by MRSA. Journal of the American College of Surgeons 2009; 208(5):981-986.
Dupeyron, C., et al. Long-term efficacy of mupirocin in the prevention of infections with methicillin-resistant *Staphylococcus aureus* in a gastroenterology unit. The Journal of Hospital Infection 2006; 63(4):385-392.
Simor, A. E. Staphylococcal decolonization: an effective strategy for prevention of infection? The Lancet Infectious Diseases 2011; 11(12):952-962.

Weidenmaier, C., et al. Differential roles of sortase-anchored surface proteins and wall teichoic acid in *Staphylococcus aureus* nasal colonization. International Journal of Medicine Microbiology 2008; 298(5-6):505-513.
Baur, S., et al. A nasal epithelial receptor for *Staphylococcus aureus* WTA governs adhesion to epithelial cells and modulates nasal colonization. PLoS Pathogens 2014; 10(5):e1004089.
Peschel, A., et al. The co-evolution of host cationic antimicrobial peptides and microbial resistance. Nature Reviews Microbiology 2006; 4(7):529-536.
Price, L. B., et al. The epidemic of extended-spectrum-beta-lactamase-producing *Escherichia coli* ST 131 is driven by a single highly pathogenic subclone H30-Rx. mBio 2013; 4(6):e00377-13.
Stegger, M., et al. Genome analysis of *Staphylococcus aureus* ST291, a double locus variant of ST398, reveals a distinct genetic lineage. PLoS One 2013; 8(5):e63008.
Price, L. B., et al. *Staphylococcus aureus* CC398: host adaptation and emergency of methicillin resistance in livestock. mBio 2012; 3(1):e00305-11.
Stegger, M., et al. Rapid differentiation between livestock-associated and livestock-independent *Staphylococcus aureus* CC398 clades. PLoS One 2013; 8(11):e79645.
Stegger, M., et al. Genome sequence of *Staphylococcus aureus* strain 11819-97, an ST80-IV European community-acquired methicillin-resistant isolate. Journal of Bacteriology 2012; 194(6):1625-1626.
Andersen, P. S., et al. Complete genome sequence of the epidemic and highly virulent CTX-M-15_Producting H30-Rx Subclone of *Escherichia coli* ST131. Genome Announcements 2013; 1(6):e00988-13.
Stegger, M., et al. Genome sequence of *Staphylococcus aureus* Strain CA-347, a USA600 Methicillin-Resistant Isolate. Genome Announcements 2013; 1(4):e00517-13.
Krismer, B., et al. Highly efficient *Staphylococcus carnosus* mutant selection system based on suicidal bacteriocin activation. Applied and Environmental Microbiology 2012; 78(4):1148-1156.
Lyon, W. J., et al. Inhibition of psychrotrophic organisms by propionicin PLG-1, a bacteriocin produced by Propionibacterium thoenii. Journal of Dairy Science 1993; 76(6):1506-1513.
Tauch, A., et al. Complete genome sequence and analysis of the multiresistant nosocomial pathogen Corynebacterium jeikeium K411, a lipid-requiring bacterium of the human skin flora. Journal of Bacteriology 2005; 187(13):4671-4682.
Faye, T., et al. The unconventional antimicrobial peptides of the classical propionibacteria. Applied Microbiology and Biotechnology 2011; 89(3):549-554.
Montalban-Lopez, M., et al. Increasing the success rate of lantibiotic drug discovery by Synthetic Biology. Expert Opinion on Drug Discovery 2012; 7(8):695-709.

\* cited by examiner

Overview of species-level classifier pipeline

SEQUENCE LISTING

```
<160> NUMBER OF SEQ ID NOS: 2

<210> SEQ ID NO 1
<211> LENGTH: 54
<212> TYPE: DNA
<213> ORGANISM: Artificial Sequence
<220> FEATURE:
<223> OTHER INFORMATION: Forward Primer
<220> FEATURE:
<221> NAME/KEY: misc_feature
<222> LOCATION: (31)..(38)
<223> OTHER INFORMATION: n is a, c, t, or g
<220> FEATURE:
<221> NAME/KEY: misc_feature
<222> LOCATION: (47)..(47)
<223> OTHER INFORMATION: d is a, g, or t
<220> FEATURE:
<221> NAME/KEY: misc_feature
<222> LOCATION: (51)..(51)
<223> OTHER INFORMATION: w is a or t

<400> SEQUENCE: 1
ccatctcatc cctgcgtgtc tccgactcag nnnnnnnncc tacgggdggc wgca         54

<210> SEQ ID NO 2
<211> LENGTH: 47
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: (39)..(40)
<223> OTHER INFORMATION: r is a or g
<220> FEATURE:
<221> NAME/KEY: misc_feature
<222> LOCATION: (43)..(43)
<223> OTHER INFORMATION: r is a or g

<400> SEQUENCE: 2
cctatcccct gtgtgccttg gcagtctcag ctgacgacrr ccrtgca              47
```

COMPOSITIONS AND METHODS FOR AUGMENTING THE NASAL MICROBIOME

CROSS-REFERENCE TO RELATED APPLICATIONS

The present application is the U.S. National Stage of International Application No. PCT/US2016/029171 filed Apr. 25, 2016, which claims the benefit of U.S. Provisional Application No. 62/152,547, filed Apr. 24, 2015, the contents of each of which are incorporated herein by reference in their entireties.

INCORPORATION-BY-REFERENCE OF MATERIAL ELECTRONICALLY FILED

The official copy of the sequence listing is submitted electronically via EFS-Web as an ASCII-formatted sequence listing with a file named "150410_236_Probiotic_ST25.txt" created on Apr. 19, 2016, and having a size of 2 kilobytes, and is filed concurrently with the specification. The sequence listing contained in this ASCII-formatted document is part of the specification and is herein incorporated by reference in its entirety.

FIELD OF INVENTION

The present invention is generally directed to compositions and methods for augmenting the nasal microbiome and more specifically directed toe compositions and methods for using probiotic candidates for controlling the growth (e.g., treating) of potentially pathogenic microorganisms within the anterior nares and/or nasal cavity.

BACKGROUND OF THE INVENTION

The human microbiome can play a key role in host susceptibility to pathogens, including in the nasal cavity, a site favored by *Staphylococcus aureus*. However, it is still unknown what determines our resident nasal microbiota—the host or the environment—and the influence of these interactions among nasal bacteria with respect to *S. aureus* colonization.

Strain typing indicates that 80-85% of *S. aureus* bacteremia cases are caused by the same strains carried in patients' anterior nares. The data linking persistent *S. aureus* nasal carriage to increased risk for invasive staphylococcal infections are robust, but we know little about the determinants of *S. aureus* nasal carriage. Likewise, there is a critical need for alternative *S. aureus* decolonization strategies that provide greater long-term success, without selecting for multi-drug-resistant *S. aureus* strains or disrupting the endogenous nasal microbiota. Four factors are key to understanding *S. aureus* nasal carriage—(i) host characteristics, (ii) environmental exposure, (iii) *S. aureus* colonization factors, and (iv) nasal microbiota. While there are known host risk factors (e.g., age), our work with the twins has shown that host genetics have limited impact on *S. aureus* nasal carriage. Likewise, human challenge studies suggest that exposure and *S. aureus* colonization factors are not sufficient to establish *S. aureus* carriage, as *S. aureus* strains from persistent carriers failed to colonize non-carriers.

In preliminary studies, the investigators found that the absolute abundances of specific nasal commensals can predict *S. aureus* carriage. Specifically, the investigators found that *Dolosigranulum* and *Simonsiella* colonization was significantly associated with *S. aureus* exclusion, while *Propionibacterium acnes* and *Corynebacterium* colonization was negatively correlated with the absolute abundance of *S. aureus* in the nasal cavity. As such, there is a need to investigate compositions and methods for treating, preventing, reducing, and/or eliminating *S. aureus* colonization of the nasal cavities to preclude potential downstream infections.

SUMMARY

In some embodiments, the invention may comprise a method of reducing colonization of a subject's anterior nares and/or nasal cavity by a microorganism. For example, the microorganism may be a potentially pathogenic organism, such as *Staphylococcus aureus* (e.g., methicillin-resistant *Staphylococcus aureus*). In some aspects, the method may include administering a pharmaceutical composition to the subject, wherein the pharmaceutical composition comprises a therapeutically effective amount of at least one probiotic. In some aspects, the pharmaceutical composition may include at least one pharmaceutically acceptable carrier. Moreover, the at least one probiotic may comprise at least one organism, such as a probiotic organism. For example, the probiotic organism may comprise at least one of *Dolosigranulum* species and *Simonsiella* species.

Other embodiments of the invention may comprise a method of treating in a subject nasal colonization by at least one pathogenic organism. For example, the pathogenic organism may comprise *Staphylococcus aureus* (e.g., methicillin-resistant *Staphylococcus aureus*). In some embodiments, the method may include administering a pharmaceutical composition to the subject, wherein the pharmaceutical composition comprises a therapeutically effective amount of at least one probiotic. In some aspects, the pharmaceutical composition may include at least one pharmaceutically acceptable carrier. For example, the pharmaceutically acceptable carrier may comprise a growth medium to sustain the at least one probiotic prior to administration to the subject. Moreover, the at least one probiotic may comprise at least one organism, such as a probiotic organism. For example, the probiotic organism may comprise at least one of *Dolosigranulum* species and *Simonsiella* species. In addition, in some aspects, the method may also include administering a therapeutically effective amount of at least one antibiotic (e.g., mupirocin). Further, in some embodiments, the method may include intranasally administering the pharmaceutical composition to the subject.

In other embodiments, the invention may include a pharmaceutical composition comprising at least one probiotic organism. For example, the at least one probiotic organism can be selected from the group consisting of *Dolosigranulum* species and *Simonsiella* species. In some aspects, the pharmaceutical composition is formulated for intranasal administration. In some aspects, the pharmaceutical composition may include at least one pharmaceutically acceptable carrier. For example, the pharmaceutically acceptable carrier may comprise a growth medium to sustain the at least one probiotic organism.

Additional objectives, advantages and novel features will be set forth in the description which follows or will become apparent to those skilled in the art upon examination of the drawings and detailed description which follows.

BRIEF DESCRIPTION OF THE DRAWINGS

FIG. 3A-3C depict nasal bacterial density and *S. aureus* absolute abundance by sex and the relationship between *S. aureus* absolute abundance and *S. aureus* culture. The scatterplot shows the higher nasal bacterial density in men than women (FIG. 3A). Individuals (non-CST1) with detectable *S. aureus* nasal colonization could be divided based on *S. aureus* absolute abundance into four categories. Women were more likely to have the two lowest categories of *S. aureus* absolute abundance (i.e., <$10^4$ and $10^4$-$10^5$), whereas men are more likely to have the middle two categories (i.e., $10^4$-$10^5$ and $10^5$-$10^6$)(FIG. 3B). Culture outcome was strongly linked to *S. aureus* absolute abundance, and each ten-fold increase in *S. aureus* absolute abundance increases the probability of positive *S. aureus* culture by 30%, which suggests that the sex difference in *S. aureus* absolute abundance might explain the lower *S. aureus* culture rates in women than men (FIG. 3C).

Figure 1A:
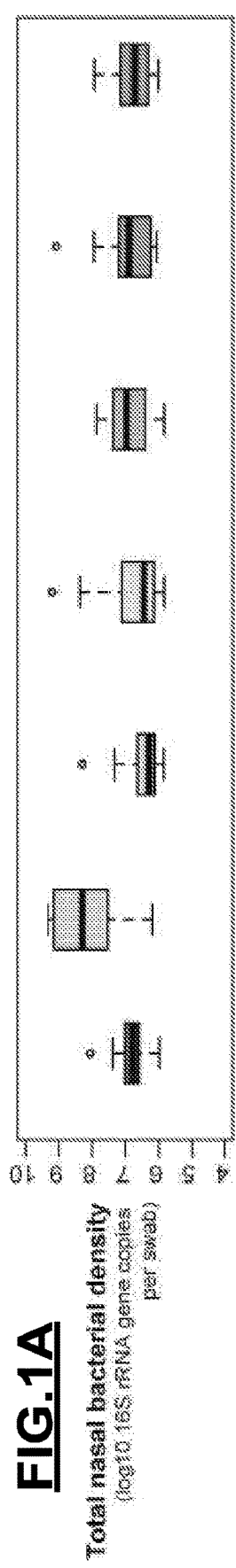
FIGS. 1A-C depict the seven nasal microbiome community state types (CSTs) and their respective bacterial density shown in boxplots and composition (in bacterial 16S rRNA gene copies per swab) shown in heatmap visualization and non-metric multidimensional scaling (nMDS) ordination plot. In the boxplots in FIG. 1A, the box of each boxplot denotes the inter-quartile range (Q2-Q3) and the corresponding median, whereas the whiskers signifies the upper and lower 1.5×IQR and the open circles denote outliers beyond the whiskers. The difference in bacterial density was significantly greater across than within CSTs (ANOVA p<0.001). In particular, CST3 had significantly lower bacterial density than all other CSTs except CST4, and CST2 had significantly higher than all other CSTs except CST6 (two-tailed Wilcoxon Rank-Sum p<0.05) (FIG. 1A). In the heatmap visualization in FIG. 1B, each participant's nasal microbiota is represented in a single column and each nasal bacterial taxon's proportional abundance is shown by row according to the color key to the left. The nasal microbiota is grouped by CSTs, as indicated by the CST color bar above. The *S. aureus* culture result of each participant is noted by the green/black color bar above. In the nMDS ordination plot in FIG. 1C, each participant's nasal microbiota (in proportional abundance) is represented by a single data point, and data points that are closer being more similar in composition than points that are farther apart. The centroids and 95% confidence ellipse for each CST is shown.

The headings used in the figures should not be interpreted to limit the scope of the claims.

DETAILED DESCRIPTION

Embodiments of the invention provide compositions and methods for the augmentation of the presence of one or more organisms on, near, adjacent to, or in a subject. For example, in some embodiments of the invention, the compositions and methods can be used to control, treat, reduce, eliminate, and/or prevent the colonization by an organism of a portion of a subject. Specifically, some aspects of the present invention can be used to control, treat, reduce, eliminate, and/or prevent the growth of organisms that may potentially negatively impact the health of the subject. Moreover, in some embodiments, the compositions and methods of the instant invention can be used to in particular locations of the subject, such as the anterior nares and/or nasal cavity.

Moreover, in some embodiments, the compositions and methods can be used to treat, reduce, eliminate, and/or prevent the colonization by potentially pathogenic microorganisms in portions of the subject. For example, in some aspects the potentially pathogenic microorganisms may be at least one of bacteria, viral particles, parasites (e.g., prokaryotic and eukaryotic parasitic organisms), etc. In particular, the microorganism may be gram positive and/or gram negative bacteria. By way of example only, in some embodiments, the organism may be a gram positive bacterium, such as *Staphylococcus aureus*.

In some embodiments, the subject can be an animal, such as a human being, a veterinary animal, such as a companion animal or livestock, or any other animal amenable to the treatment compositions and methods described herein. A subject includes any human or non-human mammal, including for example: a primate, cow, horse, pig, sheep, goat, dog, cat, or rodent, capable of being colonized by other organisms.

Some embodiments of the invention may encompass the development and administration of one or more pharmaceutical compositions. In some aspects, the pharmaceutical compositions may include one or more probiotics. As used herein, "probiotics" are active ingredients that have been known to be associated with positive health benefits in individuals, subjects, patients, etc. that receive the probiotics. In some aspects, probiotics refer to organisms, such as bacteria and yeast, which provide health benefits when administered to a subject. For example, as detailed herein, the investigators have made the unexpected determination that administration of probiotic organisms, such as *Dolosigranulum* species and *Simonsiella* species, can affect the colonization of a subject by potentially pathogenic microorganisms, such as *S. aureus*.

The invention further encompasses pharmaceutical compositions that include one or more probiotics/probiotic organisms (e.g., bacteria) as ingredients. By way of example only, in some aspects, the probiotic organisms may comprise at least one of *Dolosigranulum* species and *Simonsiella* species. In other embodiments, the probiotic organisms may comprise any other bacteria, yeast, or other organisms that are capable of providing the desired health benefits of controlling, treating, reducing, eliminating, and/or preventing the colonization of portions of the subject (e.g., the nasal cavities/anterior nares).

In one aspect, the *Dolosigranulum* species are characterized as follows: Firmicutes/"Bacilli"/"Lactobacillales"/"Carnobacteriaceae"/*Dolosigranulum*. Cells are ovoid, occurring in pairs, tetrads, or groups. Gram-stain-positive and nonmotile. Non-spore-forming. Facultatively anaerobic and catalase-negative. Growth in 6.5% NaCl. No growth at 10 or 45° C. Negative bile-esculin reaction. Gas is not produced in MRS broth. Acid is produced from d-glucose and some other sugars. Pyrrolidonylarylamidase and leucine aminopeptidase are produced. Alanine phenylalanine proline arylamidase and urease are negative. Does not deaminate arginine. Vancomycin-sensitive. Pyruvate is not utilized. Voges-Proskauer-negative. Cell-wall murein is based on L-lysine (type Lys-D-Asp). DNA G+C content (mol %): 40.5 ($T_m$). Type species: *Dolosigranulum pigrum* Aguirre, Morrison, Cookson, Gay and Collins 1994, 370$^{VP}$ (Aguirre, Morrison, Cookson, Gay and Collins 1993, 610.)

In another aspect, the *Simonsiella* species is characterized as follows: Proteobacteria/Betaproteobacteria/Neisseriales/Neisseriaceae/*Simonsiella*. Organisms that exist in characteristic multicellular filaments that are flat rather than cylindrical and often segmented into groups of eight cells. The width of an individual cell is greater than its length. The long axis of an individual cell is perpendicular to the long axis of the filament. The diameter of the filaments (the width of the individual cells) may vary from about 2.0 to 8.0 µm, and the length of filaments may vary from about 10.0 to over 50.0 µm. Individual cells within the filaments may be from about 0.5 to 1.3 µm long. In thin sections cut perpendicular to the long axis of the filament, the cells are flattened and curved to yield a crescent-shaped, convex-concave (dorsal-ventral) asymmetry. The ends of the individual filaments are rounded. Gram negative. Gliding motility of the entire filament in the direction of the long axis when the flat side of the filament is in contact with a surface. Chemoorganotrophs. Aerobic. Some may produce acid aerobically from carbohydrates. Optimal temperature: 37° C. Found in the oral cavity of warm-blooded vertebrates. The mol % G+C of the DNA is: 41-55. Type species: *Simonsiella muelleri* Schmid in Simons 1922, 504.

In yet other aspects, the *Corynebacterium* species is characterized as follows: Actinobacteria/Actinobacteria/Corynebacteriales/Corynebacteriaceae/*Corynebacterium*. Straight to slightly curved rods with tapered ends. Rods are usually short or of medium length. Club-shaped forms may be observed; sometimes ellipsoidal, ovoid or rarely, "whip handles" (see below, *Corynebacterium matruchotii*) or thinner rods with bulges (see below, *Corynebacterium sundsvallense*) observed. Snapping division produces angular and palisade arrangements of cells. Gram-stain-positive; some cells stain unevenly. Metachromatic (synonym being polyphosphate) granules may be observed for some species. Not-acid-fast (Ziehl-Neelsen stain), and no species has aerial mycelium. Nonsporeforming. All species are nonmotile. All species are catalase positive. All species are oxidase negative except for *Corynebacterium bovis*, *Corynebacterium aurimucosum*, *Corynebacterium doosanense*, and *Corynebacterium* marls (below). Many species are facultatively anaerobic and some are aerobic. Chemoorganotrophs. Some species are lipophilic. Many species produce acid from glucose and some other sugars in peptone media. Several species alkalinize citrate as sole carbon sources, but most do not. DNA G+C content (mol %): 46-74. Type species: *Corynebacterium diphtheriae* (Kruse 1886) Lehmann and Neumann 1896, 350 ("*Bacillus* diphtheria" Kruse in Flügge 1886, 225).

In some embodiments, the *Corynebacterium* species is one or more of the following species: *C. accolens*, *C. afermentans*, *C. ammoniagenes*, *C. amycolatum*, *C. argentoratense*, *C. aquaticum*, *C. auris*, *C. bovis*, *C. diphtheria*, *C. equi* (now *Rhodococcus equi*), *C. efficiens*, *C. flavescens*, *C. glucuronolyticum*, *C. glutamicum*, *C. granulosum*, *C. haemolyticum*, *C. halofytica*, *C. kroppenstedtii*, *C. jeikeium* (group JK), *C. macginleyi*, *C. matruchotii*, *C. minutissimum*, *C. parvum* (*Propionibacterium acnes*), *C. paurometabolum*, *C. propinquum*, *C. pseudodiphtheriticum* (*C. hofmannii*), *C. pseudotuberculosis*, *C. ovis*, *C. pyogenes-Trueperella pyogenes*, *C. urealyticum* (group D2), *C. renale*, *C. spec*, *C. striatum*, *C. tenuis*, *C. ulcerans*, *C. urealyticum*, and *C. xerosis*.

In certain aspects, the *Simonsiella* species, *Corynebacterium* species, and/or *Dolosigranulum* species are obtained from the oral cavity, nasal cavity, or anterior nares of warm-blooded vertebrates (e.g., humans).

Such pharmaceutical compositions may take any physical form necessary depending on a number of factors including the desired method of administration. Such physical forms include a solid, liquid, sol, gel, aerosol, or any other physical form now known or yet to be disclosed. The concept of a pharmaceutical composition including at least one probiotic organism also encompasses the at least one probiotic organism without any other additive. The physical form of the invention may affect the route of administration and one skilled in the art would know to choose a route of administration that takes into consideration both the physical form of the at least one probiotic organism and the desired result (e.g., reduced colonization of the anterior nares and/or nasal cavity). Pharmaceutical compositions that include the at least one probiotic organism may be prepared using methodology well known in the pharmaceutical art. A pharmaceutical composition that includes the at least one probiotic organism may include a second effective compound, such as an antibiotic compound (e.g., mupirocin).

Pharmaceutical compositions including the at least one probiotic organism include materials capable of modifying the physical form of a dosage unit. In one nonlimiting example, the composition includes a material that forms a coating that holds and/or supports the at least one probiotic organism. Materials that may be used in such a coating include, for example, sugar, shellac, gelatin, or any other inert coating agent.

Pharmaceutical compositions including the at least one probiotic organism may be prepared as an aerosol. Aerosols encompass a variety of systems including colloids and pressurized packages. Delivery of a composition in this form may include propulsion of a pharmaceutical composition including the at least one probiotic organism through use of liquefied gas or other compressed gas or by a suitable pump system. Aerosols may be delivered in single phase, bi-phasic, or tri-phasic systems.

Pharmaceutical compositions that include the at least one probiotic organism may also include a pharmaceutically acceptable carrier. Carriers include any substance that may be administered with the at least one probiotic organism with the intended purpose of facilitating, assisting, or helping the administration or other delivery of the active pharmaceutical agent. Carriers include any liquid, solid, semisolid, gel, aerosol or anything else that may be combined with the active pharmaceutical agent to aid in its administration. Examples include diluents, adjuvants, excipients, water, oils (including petroleum, animal, vegetable or synthetic oils.) Such carriers include particulates such as a tablet or powder, liquids such as an oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or diglycerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents. In some embodiments of the invention, the pharmaceutically acceptable carrier can comprise a growth medium that can support the growth and/or static existence of the at least one probiotic organism in the context of the pharmaceutical composition prior to administration of the pharmaceutical composition to the subject. For example, the pharmaceutical composition can comprise one or pharmaceutically acceptable carrier to provide sufficient sustenance for the at least one probiotic organism that are also compatible with the desired route of administration (e.g., intranasal administration).

The pharmaceutical composition including the active pharmaceutical agent may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in "Remington's Pharmaceutical Sciences" by E. W. Martin, hereby incorporated by reference in its entirety.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intranasal, intracerebral, intraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

The term "therapeutically effective amount" as used herein means that the amount/number of colony forming units of the at least one probiotic organism contained in the pharmaceutical composition administered that is of sufficient quantity to achieve the intended purpose, such as, in this case, to control, treat, reduce, eliminate, and/or prevent the colonization of the subject by a potentially pathogenic microorganism, such as *S. aureus*. The addition of a therapeutically effective amount of the pharmaceutical composition encompasses any method of dosing of a composition. Dosing of the at least one probiotic organism may include single or multiple administrations of any of a number of pharmaceutical compositions that include the at least one probiotic organism as an active ingredient. Examples include a single administration, a course of treatment involving several treatments on a regular or irregular basis, multiple administrations for a period of time until a diminution of colonization is achieved, preventative treatments applied prior to the instigation of colonization, or any other dosing regimen known in the art or yet to be disclosed that one skilled in the art would recognize as a potentially effective regimen. A final dosing regimen including the regularity of and mode of administration will be dependent on any of a number of factors including but not limited to the subject being treated; the severity of the affliction; the manner of administration, the stage of colonization, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Examples

The familiarity with the exterior of the nose belies the intriguing puzzle within. Individuals can have distinctive susceptibilities to nasal colonization by *Staphylococcus aureus*, a major pathogen (1); yet, it also appears that host genetics is not a significant determinant of *S. aureus* nasal colonization (2). One potential explanation for this dissonance is that individuals' susceptibility to *S. aureus* nasal colonization is driven by an environmentally determined phenotype. To satisfy this explanation, the phenotype should have limited association with host genetics, but it should predict *S. aureus* nasal colonization. As the human microbiome is increasingly considered a host phenotype (3-5), the investigators examined the potential role of nasal microbiota in *S. aureus* nasal colonization. Testing this hypothesis provided useful insight into the malleability of nasal microbiota and explanations for previous contradictory findings regarding *S. aureus*' negative association with nasal bacteria such as *Propionibacterium* and *Staphylococcus epidermidis* (6-10).

To test this hypothesis, the investigators enrolled and collected nasal swabs from 46 monozygotic and 43 dizygotic twin pairs (Table 1), which were cultured for *S. aureus* using standard non-selective media as previously described (2). The investigators measured nasal bacterial density (i.e., the amount of nasal bacteria present) using a broad-coverage quantitative PCR (11) and characterized nasal microbiota composition (i.e., the types and proportions of bacteria present in the nasal microbiota) by 16S rRNA gene-based sequencing and taxonomic classification, as previously described (12), with some modifications. Using the taxonomically-classified sequence data, the investigators calculated the proportional abundance for each nasal bacterial taxon as: (Number of sequences assigned to the taxon from the sample)/(Total number of sequences from the sample), which the investigators combined with nasal bacterial density to calculate taxon absolute abundance as: (Proportional abundance of the taxon from the sample)×(nasal bacterial density of the sample) (12).

TABLE 1

*Atopic diseases include asthma, atopic dermatitis, and allergy.

| | Monozygotic (n = 46 pairs) | Dizygotic Same Sex (n = 23 pairs) | Dizygotic Opposite Sex (n = 20 pairs) |
|---|---|---|---|
| | Number of individuals or twin pairs (%) | | |
| Age | | | |
| 50-54 yr | 12 (26.1) | 0 (0.0) | 0 (0.0) |
| 55-59 yr | 13 (28.3) | 0 (0.0) | 0 (0.0) |
| 60-64 yr | 7 (15.2) | 4 (17.4) | 1 (5.0) |
| 65-69 yr | 9 (19.6) | 4 (17.4) | 11 (55.0) |
| 70-74 yr | 3 (6.5) | 12 (52.2) | 7 (35.0) |
| 75-79 yr | 2 (4.4) | 3 (13.0) | 1 (5.0) |

TABLE 1-continued

*Atopic diseases include asthma, atopic dermatitis, and allergy.

| | Monozygotic (n = 46 pairs) | Dizygotic Same Sex (n = 23 pairs) | Dizygotic Opposite Sex (n = 20 pairs) |
|---|---|---|---|
| Sex | | | |
| Female | 25 (54.4) | 16 (69.6) | 20 (100.0) |
| Male | 21 (45.6) | 7 (30.4) | |
| Smoking | | | |
| Smoker | 14 (15.2) | 9 (19.6) | 10 (25.0) |
| Concordance | 40 (87.0) | 16 (69.6) | 12 (60.0) |
| History of Atopic Disease* | | | |
| Yes | 27 (29.3) | 14 (30.4) | 13 (32.5) |
| Concordance | 31 (86.1) | 15 (65.2) | 15 (75.0) |
| History of Psoriasis | | | |
| Yes | 8 (9.7) | 2 (4.3) | 5 (12.5) |
| Unknown | 1 (2.2) | 1 (4.3) | 2 (2.5) |
| Concordance | 39 (84.8) | 20 (87.0) | 14 (70.0) |
| Farm Exposure | | | |
| Yes | 1 (1.1) | 2 (4.3) | 1 (2.5) |
| Unknown | 0 (0.0) | 2 (8.7) | 0 (0.0) |
| Concordance | 45 (97.8) | 21 (91.3) | 19 (95.0) |

Figure 1C:
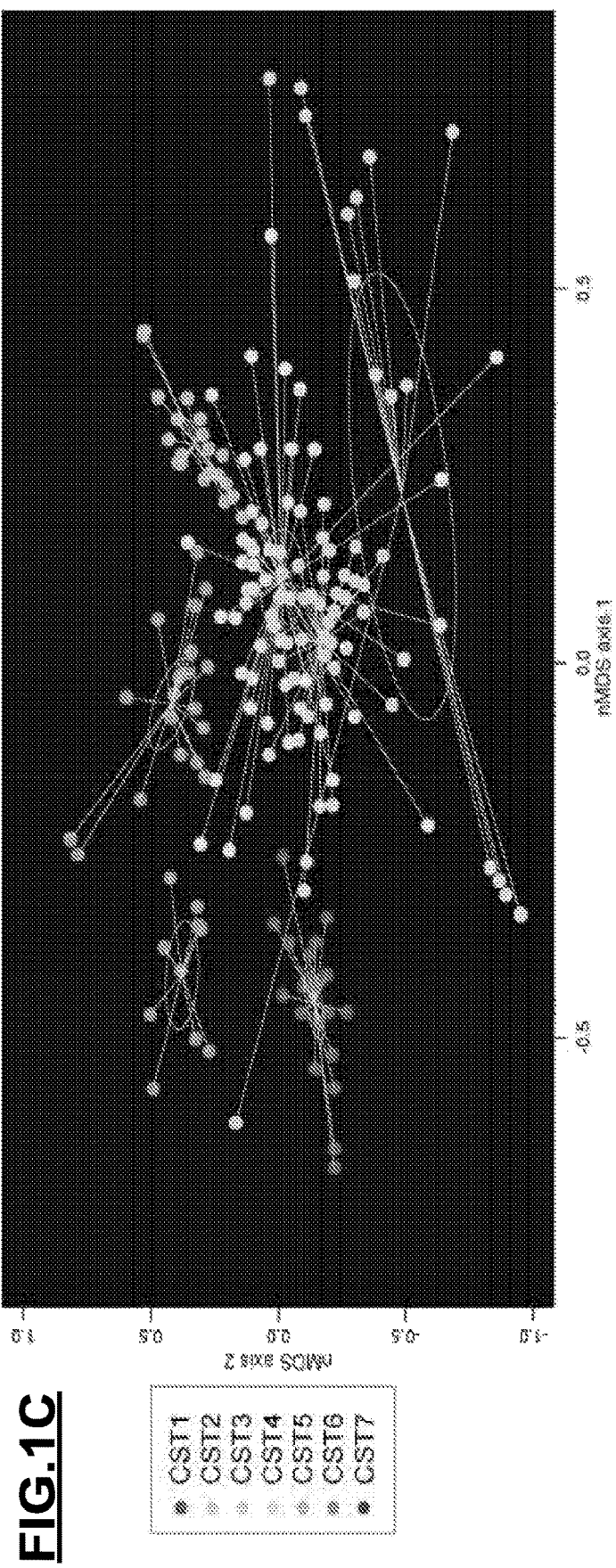
Figure 1B:
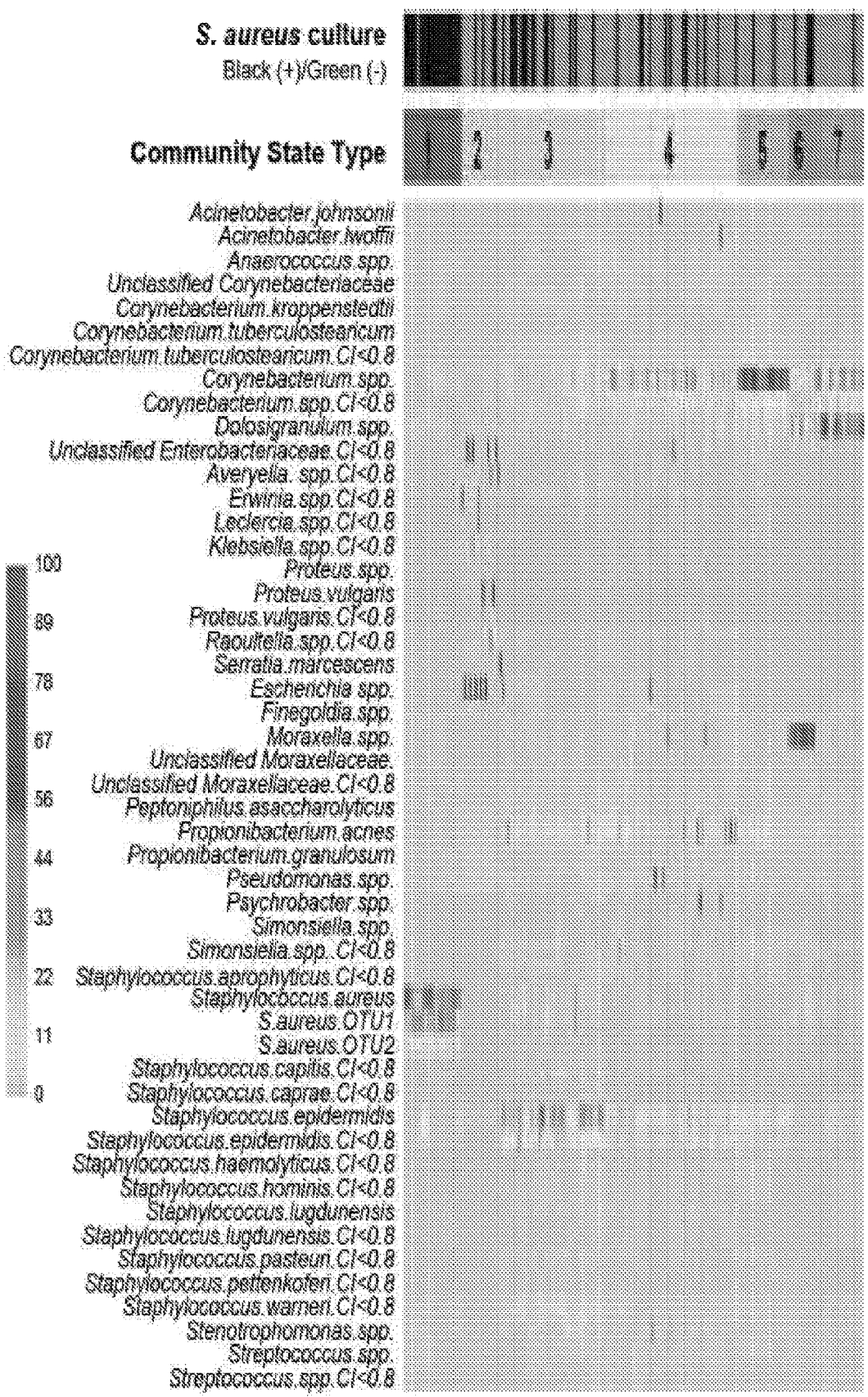

The nasal bacterial density and microbiota composition were highly diverse among the 178 healthy, community-dwelling middle-aged adults. The median nasal bacterial density was $4.4 \times 10^6$ 16S rRNA gene copies per swab, and it spanned nearly four orders of magnitude, from $6.7 \times 10^5$ to $2.1 \times 10^9$ 16S rRNA gene copies per swab (Inter-Quartile Range (IQR): $1.6 \times 10^6$-$1.7 \times 10^7$). Many bacteria were found in large proportions of subjects, such as *Corynebacterium* (n=157/178, 88.2%), *Propionibacterium acnes* (n=149/178, 83.7%), *Staphylococcus epidermidis* (n=161/178, 90.4%), but proportional abundance varied substantially across individuals, contributing to distinctive microbiota compositions. The investigators identified seven major nasal community state types (CST1-7) among our participants (FIGS. 1A-C). Each CST had uniquely high prevalence and proportional abundance of specific nasal bacteria, as identified by indicator analysis: *S. aureus* defined CST1, Enterobacteriaceae—including *Escherichia* spp., *Proteus* spp., and *Klebsiella* spp.—defined CST2, *Staphylococcus epidermidis* defined CST3, *Proprionibacterium* spp. defined CST4, *Corynebacterium* spp. defined CST5, *Moraxella* spp. defined CST6, and *Dolosigranulum* spp. defined CST7 (Table 2). The most prevalent nasal CST was CST4 (n=51/178, 28.7%), followed by CST3 (n=40/178, 22.5%) and CST1 (n=22/178, 12.4%). CST6 was the least common, with only 5.6% prevalence (n=10/178) (Table 3). Thus, this study revealed distinctive nasal CSTs and greater nasal microbiota heterogeneity than previously reported (6-10), particularly among Enterobacteriaceae, of which *Proteus* and *Serratia* were not previously known to dominate the nasal microbiota.

TABLE 2

*FDR-adjusted: adjusted by false-discovery rate

| CST | Indicator Taxa | Average Proportional Abundance (SD) | Indicator Value | Unadjusted p-value | FDR-adjusted* p-value |
|---|---|---|---|---|---|
| 1 | Staphylococcus aureus | 0.38 (0.13) | 0.82 | 1.00E−04 | 3.57E−04 |
|   | Staphylococcus aureus CI < 0.8 | 0.31 (0.10) | 0.80 | 1.00E−04 | 3.57E−04 |
|   | Staphylococcus auricularis CI < 0.8 | 0.06 (0.04) | 0.84 | 1.00E−04 | 3.57E−04 |
|   | Staphylococcus lugdunensis CI < 0.8 | 0.01 (0.01) | 0.42 | 3.00E−04 | 8.82E−04 |
| 2 | Escherichia unclassified | 0.29 (0.44) | 0.46 | 3.00E−04 | 8.82E−04 |
|   | Enterobacteriaceae unclassified CI < 0.8 | 0.15 (0.27) | 0.37 | 7.00E−04 | 1.84E−03 |
|   | Klebsiella CI < 0.8 | 0.04 (0.08) | 0.43 | 1.80E−03 | 4.29E−03 |
|   | Proteus vulgaris CI < 10.8 | 0.03 (0.07) | 0.23 | 2.70E−03 | 5.87E−03 |
|   | Proteus vulgaris | 0.09 (0.22) | 0.19 | 5.90E−03 | 1.23E−02 |
|   | Raoultella CI < 0.8 | 0.04 (0.10) | 0.17 | 2.65E−02 | 4.88E−02 |
|   | Erwinia CI < 0.8 | 0.08 (0.16) | 0.30 | 3.55E−02 | 5.92E−02 |
|   | Averyella CI < 0.8 | 0.06 (0.16) | 0.12 | 4.24E−02 | 6.84E−02 |
| 3 | Staphylococcus epidermidis | 0.26 (0.11) | 0.50 | 1.00E−04 | 3.57E−04 |
|   | Staphylococcus capitis CI < 0.8 | 0.02 (0.01) | 0.43 | 1.00E−04 | 3.57E−04 |
|   | Staphylococcus caprae CI < 0.8 | 0.01 (0.01) | 0.41 | 1.00E−04 | 3.57E−04 |
|   | Staphylococcus epidermidis CI < 0.8 | 0.14 (0.06) | 0.49 | 1.00E−04 | 3.57E−04 |
|   | Staphylococcus pettenkoferi CI < 0.8 | 0.005 (0.004) | 0.41 | 1.00E−04 | 3.57E−04 |
|   | Staphylococcus warneri CI < 0.8 | 0.03 (0.02) | 0.44 | 1.00E−04 | 3.57E−04 |
|   | Staphylococcus hominis CI < 0.8 | 0.02 (0.02) | 0.44 | 3.00E−04 | 8.82E−04 |
|   | Staphylococcus pasteuri CI < 0.8 | 0.01 (0.01) | 0.35 | 5.00E−04 | 1.39E−03 |
|   | Anaerococcus unclassified | 0.01 (0.01) | 0.25 | 1.76E−02 | 3.52E−02 |
|   | Stenotrophomonas unclassified | 0.05 (0.07) | 0.24 | 2.04E−02 | 3.92E−02 |
|   | Staphylococcus haemolyticus CI < 0.8 | 0.01 (0.01) | 0.28 | 2.73E−02 | 4.88E−02 |
| 4 | Propionibacterium acnes | 0.12 (0.15) | 0.35 | 2.70E−03 | 5.87E−03 |
| 5 | Corynebacteriaceae unclassified | 0.01 (0.02) | 0.25 | 3.48E−02 | 5.92E−02 |
|   | Corynebacterium tuberculostearicum | 0.01 (0.01) | 0.52 | 1.00E−04 | 3.57E−04 |
|   | Corynebacterium unclassified | 0.54 (0.12) | 0.51 | 1.00E−04 | 3.57E−04 |
|   | Corynebacterium unclassified CI < 0.8 | 0.10 (0.04) | 0.48 | 1.00E−04 | 3.57E−04 |
|   | Corynebacterium tuberculostearicum CI < 0.8 | 0.02 (0.01) | 0.32 | 1.30E−03 | 3.25E−03 |
| 6 | Moraxella unclassified | 0.55 (0.10) | 0.81 | 1.00E−04 | 3.57E−04 |
| 7 | Dolosigranulum unclassified | 0.41 (0.20) | 0.56 | 1.00E−04 | 3.57E−04 |

TABLE 3

*Comparison of nasal CST distribution in men versus women resulted in $\chi^2 = 7.8$, df = 6, p = 0.25

| | Nasal bacterial density | | Sex* | | |
|---|---|---|---|---|---|
| | Median | Q1-Q3 | Female (n = 102) | Male (n = 76) | Total (n = 178) |
| | 16S rRNA gene copies per swab | | Number (%) | | |
| CST1 | 5.33E+06 | 4.01E+06-9.39E+06 | 16 (15.7) | 6 (7.9) | 22 |
| CST2 | 4.10E+07 | 2.03E+07-3.88E+08 | 10 (9.8) | 6 (7.9) | 16 |
| CST3 | 2.06E+06 | 1.49E+06-5.28E+06 | 25 (24.5) | 15 (19.7) | 40 |
| CST4 | 2.22E+06 | 1.10E+06-1.81E+08 | 27 (26.4) | 24 (31.5) | 51 |
| CST5 | 4.81E+06 | 2.00E+06-1.46E+07 | 9 (8.8) | 11 (14.5) | 20 |
| CST6 | 1.37E+07 | 2.46E+06-1.78E+07 | 4 (3.9) | 6 (7.9) | 10 |
| CST7 | 5.15E+06 | 2.13E+06-1.24E+07 | 11 (10.8) | 8 (10.5) | 19 |

TABLE 4

| | MZ versus DZ | | MZ versus randomly-selected, same sex non-twin pairs | | |
|---|---|---|---|---|---|
| | Female | Male | Female | Male | Overall |
| Jaccard's | | | | | |
| Mean | −0.037 | 0.109 | −0.064 | −0.041 | −0.049 |
| 2.5% CL | −0.15 | −0.047 | −0.178 | −0.131 | −0.122 |
| 97.5% CL | 0.07 | 0.251 | 0.047 | 0.063 | 0.022 |
| Bray-Curtis | | | | | |
| Mean | −0.033 | 0.109 | −0.076 | −0.061 | −0.063 |
| 2.5% CL | −0.166 | −0.082 | −0.216 | −0.182 | −0.154 |
| 97.5% CL | 0.112 | 0.279 | 0.055 | 0.057 | 0.026 |
| Euclidean | | | | | |
| Mean | −130257 | 94896 | −50014 | −26934 | −32343 |
| 2.5% CL | −388536 | 13490 | −221823 | −169013 | −145271 |
| 97.5% CL | 76979 | 235086 | 95268 | 118081 | 78943 |

Was Nasal Microbiota Significantly Associated with Host Genetics?

Figure 2A:
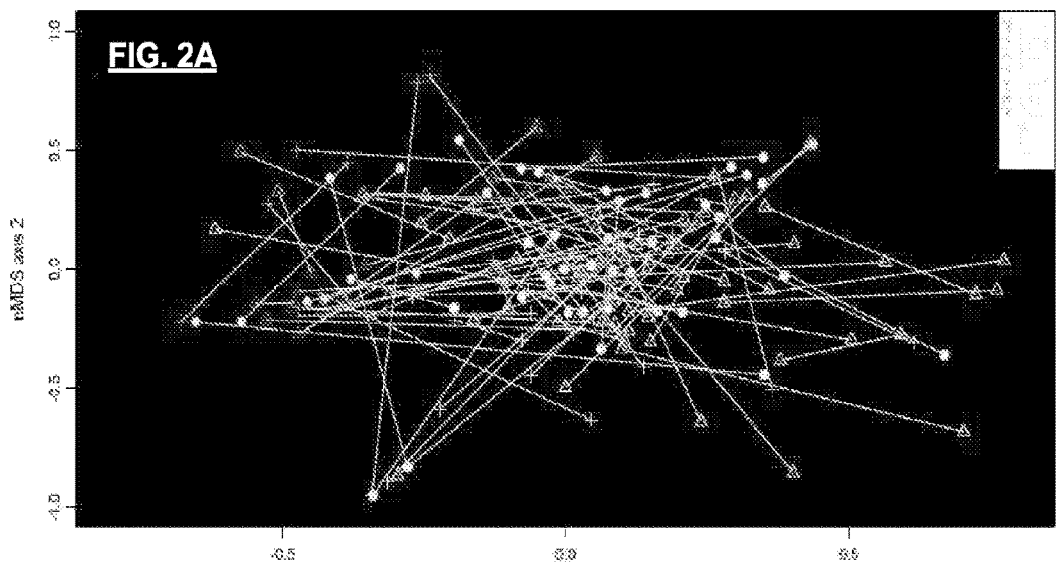
FIG. 2A-C shows that nasal microbiome is not fixed by host genetics and therefore can be modified through external manipulations such as probiotics. Specifically, the FIG. 2A-C depict data illustrating the limited correlation of nasal microbiota composition among monozygotic and among same-sex and opposite-sex dizygotic twin pairs in non-metric multidimensional scaling (nMDS) ordination plots. In nMDS plots, each data point represents an individual's microbiota at one time point. Each twin pair is connected by a solid line, which showed that the nasal microbiota in monozygotic twin pairs (FIG. 2A) had low CST concordance, as same-sex (FIG. 2B) and opposite-sex dizygotic twins (FIG. 2C).
Figure 2B:
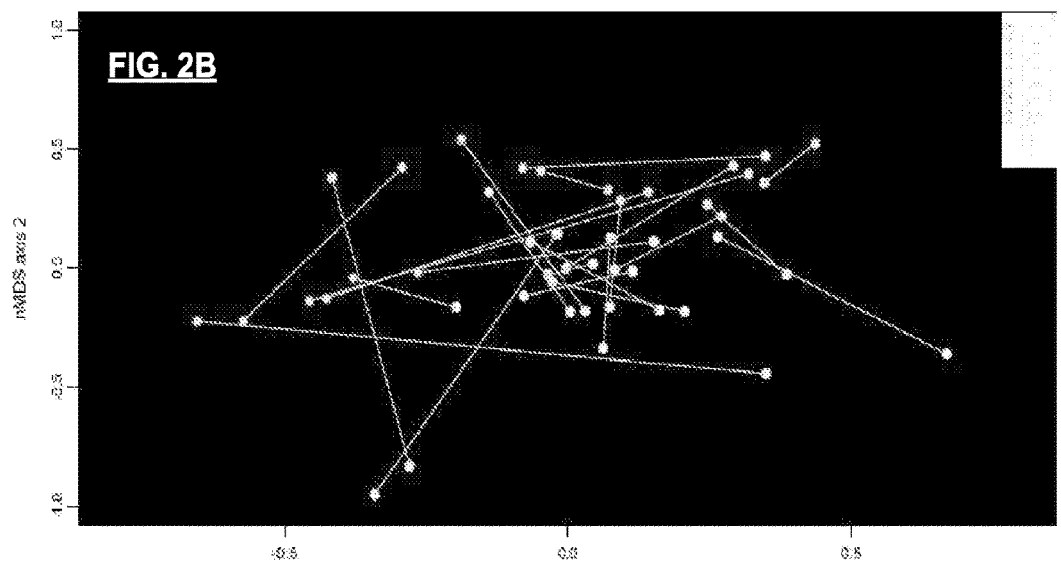
Figure 2C:
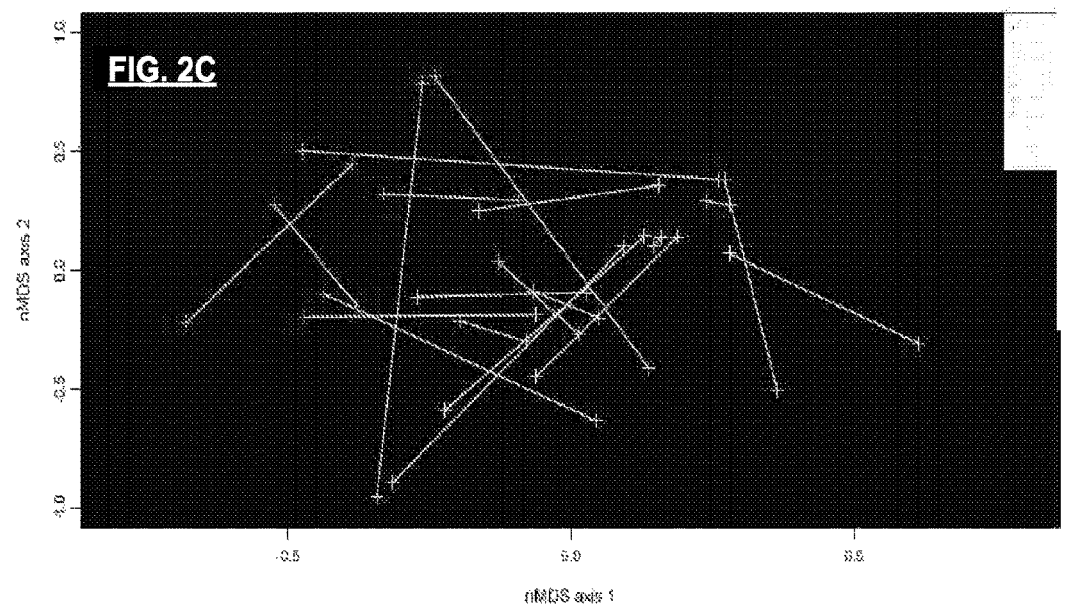

Host genetics played no significant role in nasal microbiota composition. Among monozygotic twin pairs, only 26.1% had the same nasal CSTs (n=12/46) (FIG. 1C), which was comparable to the 25.6% among dizygotic twin pairs (n=11/43) (FIG. 2A-2C). The investigators confirmed the limited similarity in nasal microbiota composition of monozygotic twin pairs by ecological distance-based analysis, where we found that nasal microbiota of monozygotic twins were not more similar than all or same-sex dizygotic twins, or than unrelated same-sex pairs (Table 4).

In contrast, host genetics and nasal bacterial density were significantly linked. Nasal bacterial densities of monozygotic twin pairs were significantly more correlated than dizygotic twin pairs (Sex- and age-adjusted Intra-class Correlation Coefficient (ICC) in MZ twins: 0.42, 95% Cl: 0.12-0.65 and for DZ twins: −0.06, 95% CI −0.35-0.23). The variations in nasal bacterial density were best explained by a model that comprised additive genetic and non-shared environmental effects (Table 5). Approximately 30% of the variation in nasal bacterial density was heritable (95% Cl: 6%-54%) with a large non-shared environmental effect of 70% (95% Cl: 46%-94%).

Figures 3A, 3B, 3C:
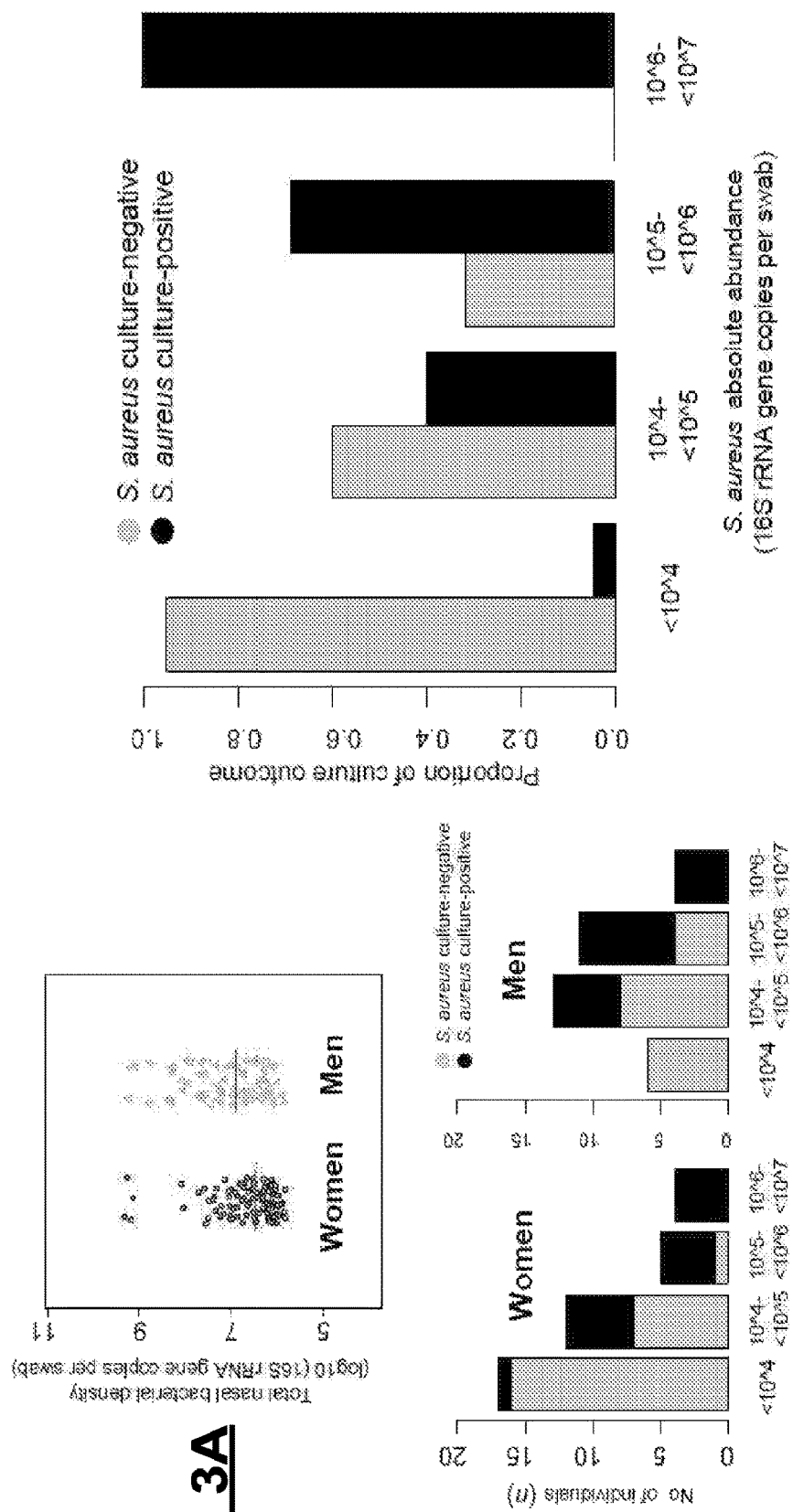
FIGS. 3A-3C shows that total nasal bacterial density varies significantly based on sex and therefore men and women will likely require different probiotic formulations. Specifically

The sex of the host also significantly influenced nasal bacterial density. On average, nasal bacterial density of women was approximately half that of men (Women Median: $2.97 \times 10^6$ 16S rRNA gene copies per swab, IQR: $1.33 \times 10^6$-$9.11 \times 10^6$; Men Median: $7.94 \times 10^6$, IQR: $2.20 \times 10^6$-$4.30 \times 10^7$) (Wilcoxon rank-sum p<0.001) (FIG. 3A, Table 6). Smoking and the history of atopic diseases or psoriasis had no significant effect on nasal bacterial density (Smoking p=0.61, Psoriasis p=0.22, Psoriasis p=0.22) (Table 6).

The types of nasal bacteria present were also associated with nasal bacterial density, as indicated by the significantly different densities across CSTs (ANOVA p<0.001). Bacterial density was highest in the two least prevalent CSTs: Enterobacteriaceae-dominated CST2 and *Moraxella*-dominated CST6; in contrast, bacterial densities were lowest in the two most prevalent CSTs: CST3 and CST4 (Table 3). The distinctive densities across nasal CSTs indicate that density may be a unique feature of the individual nasal CSTs.

Figure 5A:
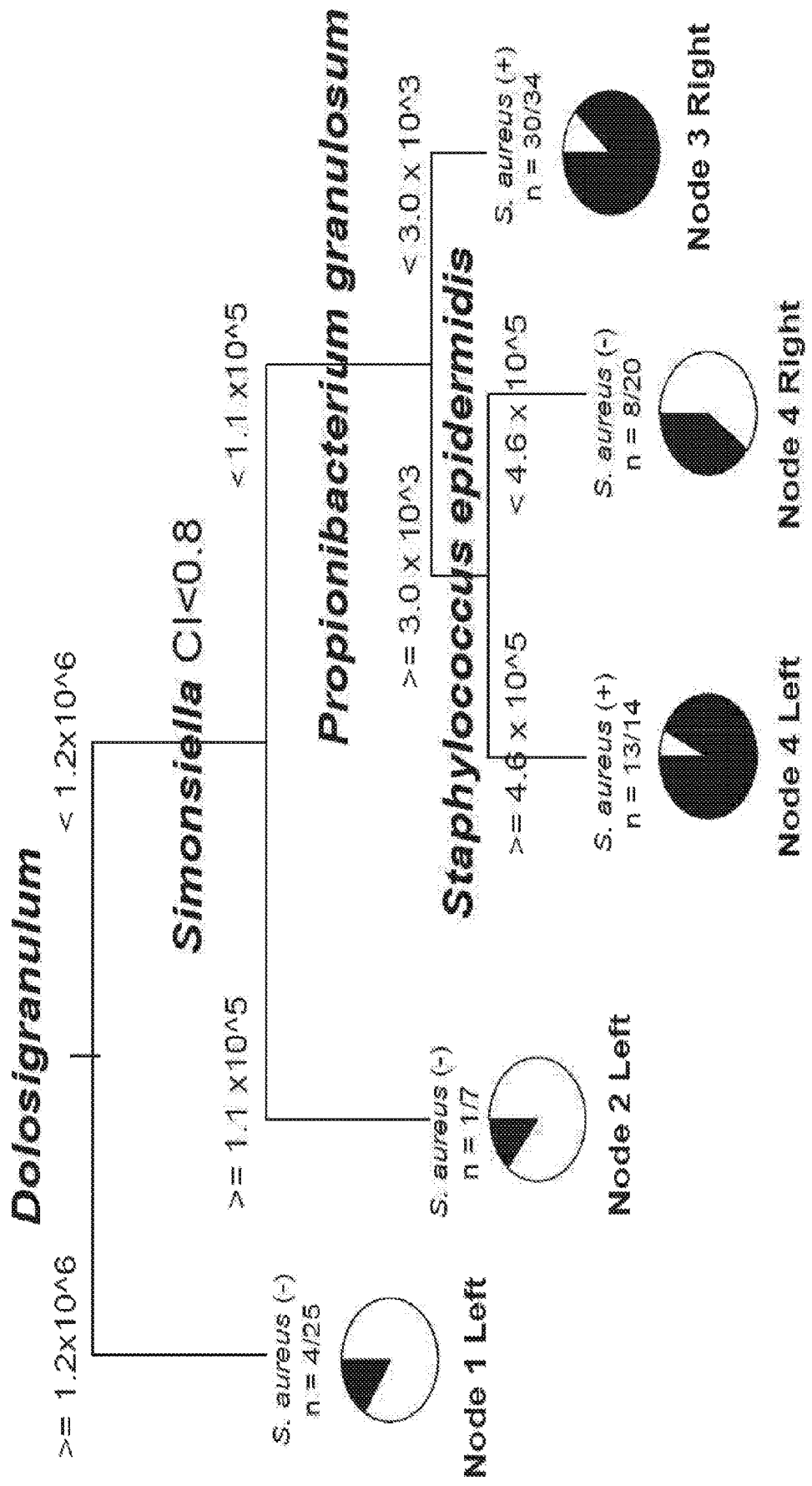
FIGS. 5A-B depict results from decision tree model derivation and validation showing threshold-dependent relationships between the absolute abundances of nasal commensals and *S. aureus* presence/absence. A model predicting *S. aureus* presence/absence was derived using a randomly drawn group of 100 (FIG. 5A); it showed that the most informative split was a threshold of $1.2 \times 10^6$ *Dolosigranulum* 16S rRNA gene copies per swab. Having above-threshold *Dolosigranulum* predicts absence of *S. aureus* (n=4/25, 16.0%), as compared to *S. aureus* nasal colonization rate in the overall derivation group (n=56/100, 56%). *Simonsiella* had a similarly negative relationship to *S. aureus*, where among individuals who had below-threshold abundance of *Dolosigranulum*, having ≥$1.1 \times 10^5$ *Simonsiella* predicts absence of *S. aureus* (n=1/7, 14.3%). Validation testing using 10 randomly drawn groups of 100 supported that threshold-based relationships between *Dolosigranulum*, *Simonsiella*, *P. granulosum*, and *S. epidermidis* and *S. aureus* presence/absence (FIG. 5B).
Figure 5B:
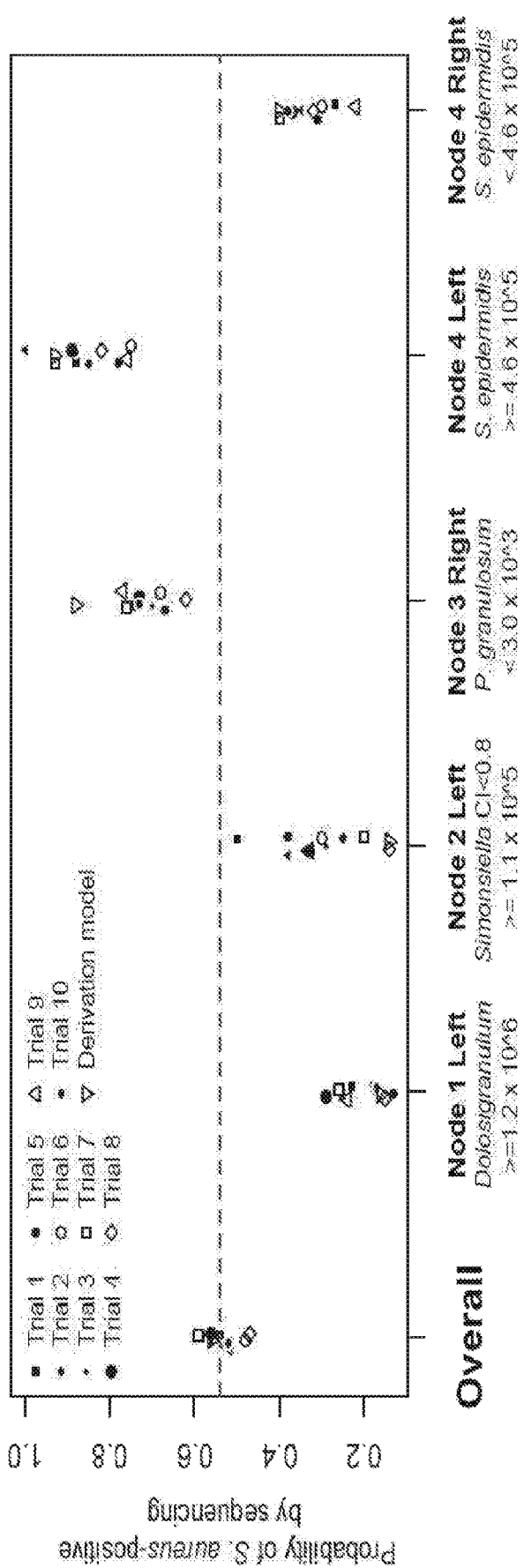
Figures 6A, 6B:
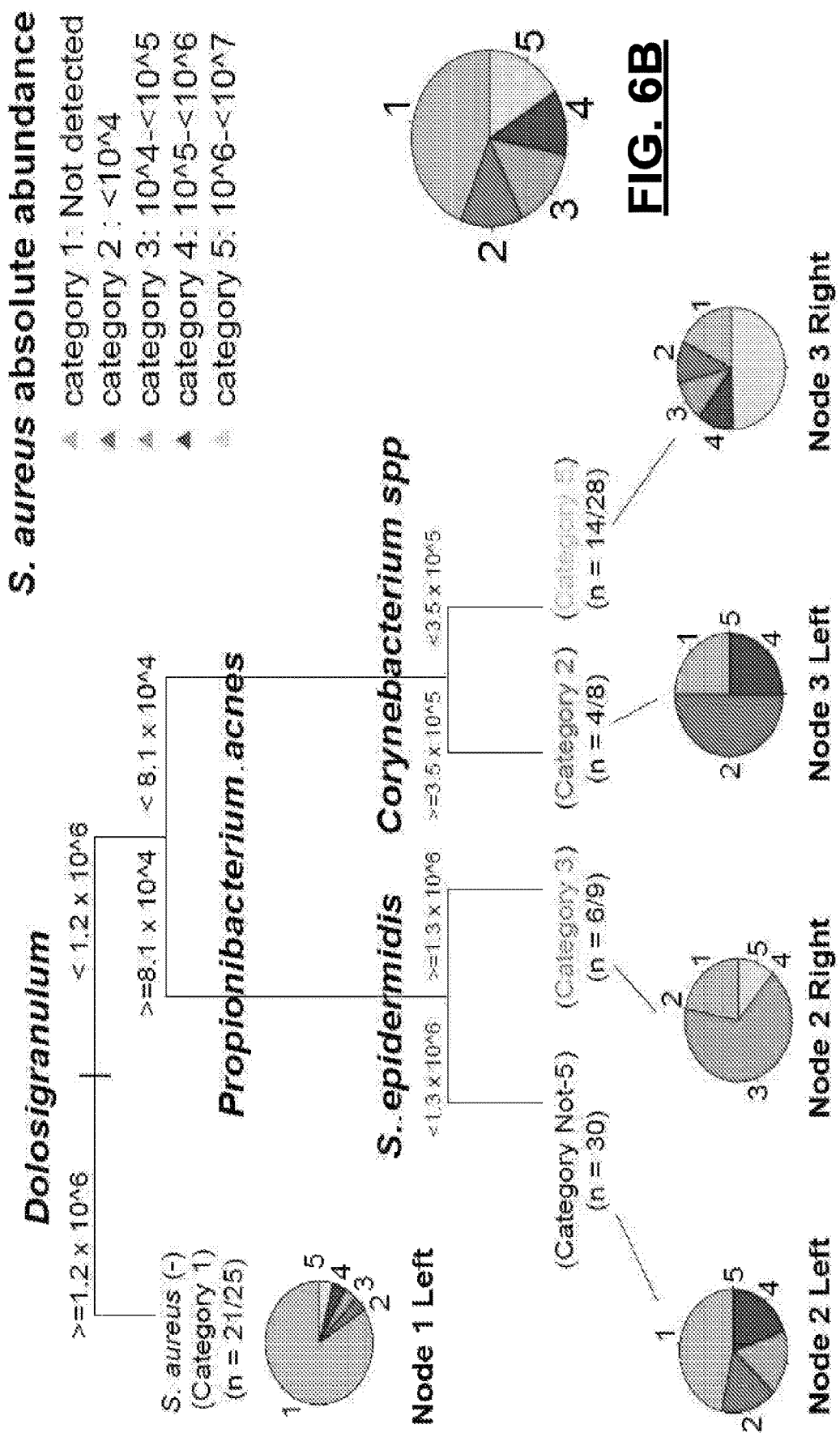
FIGS. 6A-B depict results from decision tree model derivation and validation showing threshold-dependent relationships between the absolute abundances of nasal commensals and *S. aureus*. Absolute abundance of *S. aureus* can be divided into five categories, ranging from Category 1 (i.e., not detected) to Category 5 (i.e., $10^6$-$10^7$ *S. aureus* 16S rRNA gene absolute abundance). The *S. aureus* absolute abundance categories for the derivation group of 100 are as shown (FIG. 6B), which was used to build a model to predict *S. aureus* absolute abundance (FIG. 6A). The model showed that the most informative split was a threshold of $1.2 \times 10^6$ *Dolosigranulum* 16S rRNA gene copies per swab, which predicted Category 1 (n=21/25, 84.0%) (Node 1 Left). *Corynebacterium* had a similarly negative relationship to *S. aureus* absolute abundance, where among individuals who had below-threshold abundance of *Dolosigranulum* and *P. acnes*, having ≥$3.5 \times 10^5$ *Corynebacterium* predicts low *S. aureus* absolute abundance, i.e., Category 2 (Node 3 Left), whereas having <$3.5 \times 10^5$ *Corynebacterium* predicts high *S. aureus* absolute abundance, i.e., Category 5 (Node 3 Right). In contrast, absolute abundance of *S. epidermidis* and *S. aureus* were positively correlated among individuals with low *Dolosigranulum* and high *P. acnes*. Validation testing using 10 randomly drawn groups of 100 supported that threshold-based relationships between *Dolosigranulum*, *P. acnes*, *S. epidermidis*, *Corynebacterium* and *S. aureus* absolute abundance (FIG. 6C).
Figure 6C:
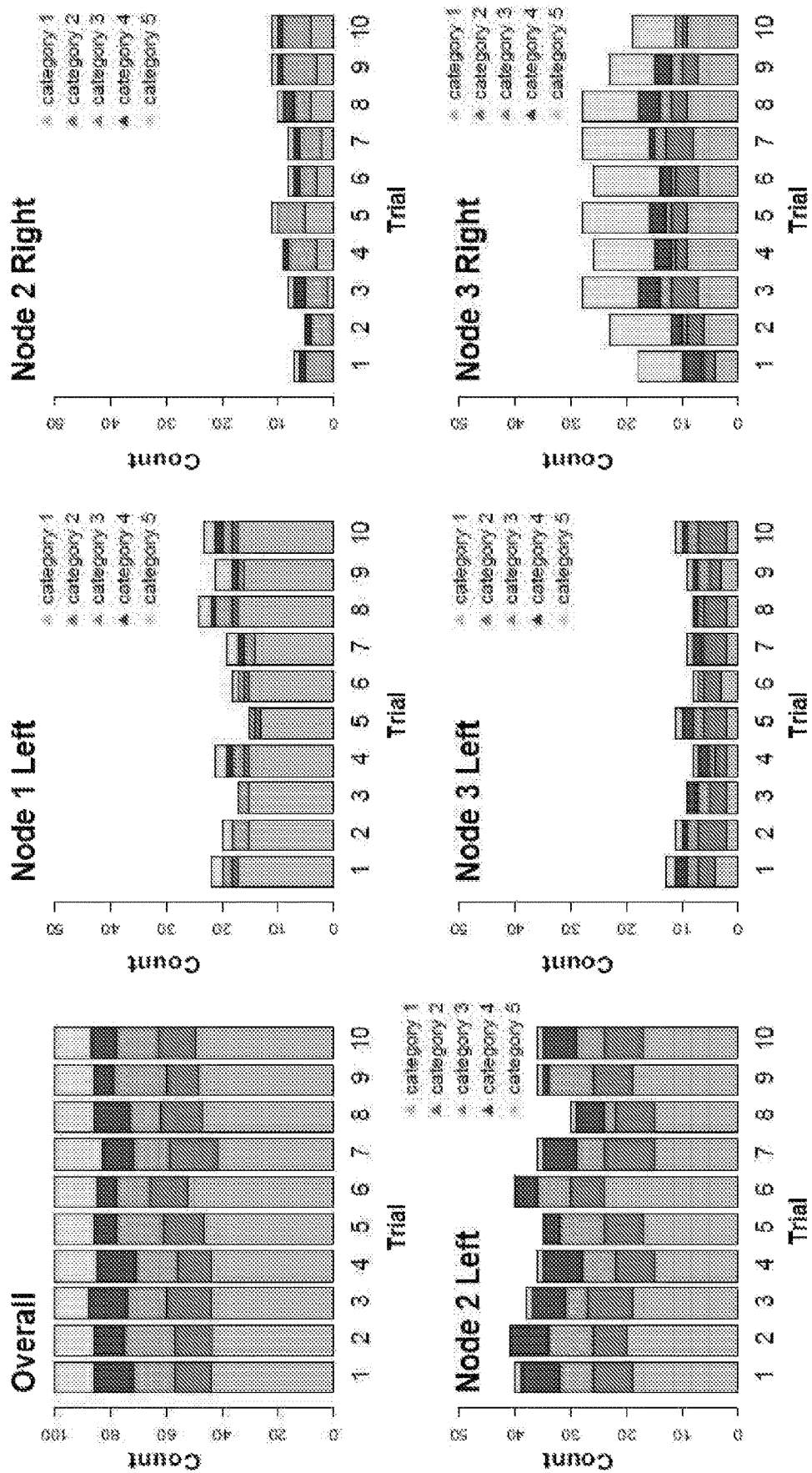
Figure 7:
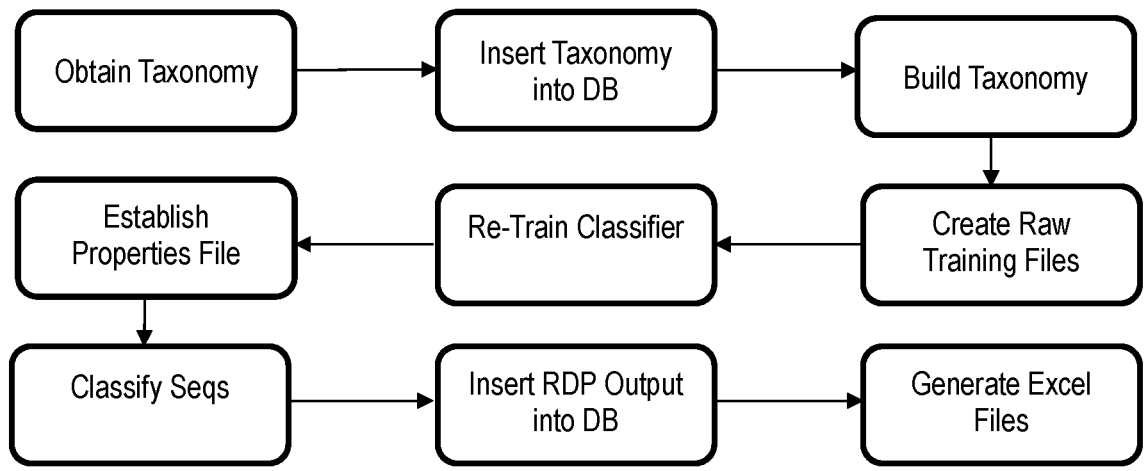
FIG. 7 depicts a species-level classifier pipeline.

The sex difference in nasal bacterial densities was not due to men's propensity for high-density nasal CSTs. The investigators found no significant sex difference in nasal CST distribution ($\chi 2 = 7.8$, df=6, p=0.25) (Table 3). Overall, men had higher nasal bacterial density than women, irrespective of nasal CSTs (p<0.001) (Table 7).

lated and supported the threshold-dependent relationships between *S. aureus* and other nasal taxa from both models (FIG. 5B, FIG. 6C). Thus, these findings indicate that nasal taxa determine *S. aureus* nasal colonization through two types of interactions: by exclusion and by limiting *S. aureus* abundance. Ecologically, these relationships may manifest as a result of competition or common sorting along an abiotic axis.

Culture-Negative *S. aureus* Nasal Colonization.

In the current study, men and women did not differ in *S. aureus* nasal colonization rates by DNA sequencing (Women 52.9%; Men 52.6%). This contradicted previous culture-based studies that have showed men are more likely to be colonized by *S. aureus* (2, 13-15). However, this discrepancy could be explained by the higher absolute abundance of *S. aureus* in men and its influence on culture outcomes. Specifically, except in CST1, women frequently had 10- to 100-fold lower *S. aureus* absolute abundance than men (FIG. 3B). At the same time, *S. aureus* absolute abundance had a strong positive link to culture outcome. Each 10-fold increase in *S. aureus* increased the probability of a positive culture by 30.0% ($r^2=0.33$, p<0.001) (FIG. 3C). After adjusting for sex and other host factors, *S. aureus* absolute abundance was the key determinant of culture-positive *S. aureus* nasal colonization ($r^2=0.33$, p<0.05). This suggests

TABLE 5

| Models | Correlation within MZ | Correlation within DZ | A (%) | D (%) | C (%) | E (%) | log likelihood | P-value* | AIC |
|---|---|---|---|---|---|---|---|---|---|
| U** | 0.42 (0.12, 0.65) | −0.06 (−0.35, 0.23) | 0 | 0 | 0 | 0 | −205.7 | | 423.4 |
| ACE | 0.30* (0.05, 0.51) | 0.15 (0.03, 0.27) | 30 (6, 54) | 0 | 0 (−, −) | 70 (46, 94) | −207.2 | | 426.5 |
| ADE | 0.38 (0.13, 0.59) | 0.1 (0.04, 0.15) | 0 (−, −) | 38 (15.62) | 0 | 61.9 (38, 85) | −206.4 | | 424.8 |
| AE§ | 0.30* (0.05, 0.51) | 0.15 (0.03, 0.27) | 30 (6, 54) | 0 | 0 | 70 (46, 94) | −207.2 | 0.19 | 424.5 |
| E | | | 0 | 0 | 0 | 1 | −209.3 | 0.04 | 426.6 |

*P-value from comparing forcing correlation of MZ to be twice the correlation of DZ in the polygenetic model. The AE model was compared to ADE model and the E model was compared to the AE model.
**U model is a model with equal regression, intercept, and residual variance for twin 1 and twin 2 as well as for MZ and DZ twins
§The AE model was selected as the final model.

Can the Nasal Microbiota Predict *S. aureus* Nasal Colonization?

Figure 4A:
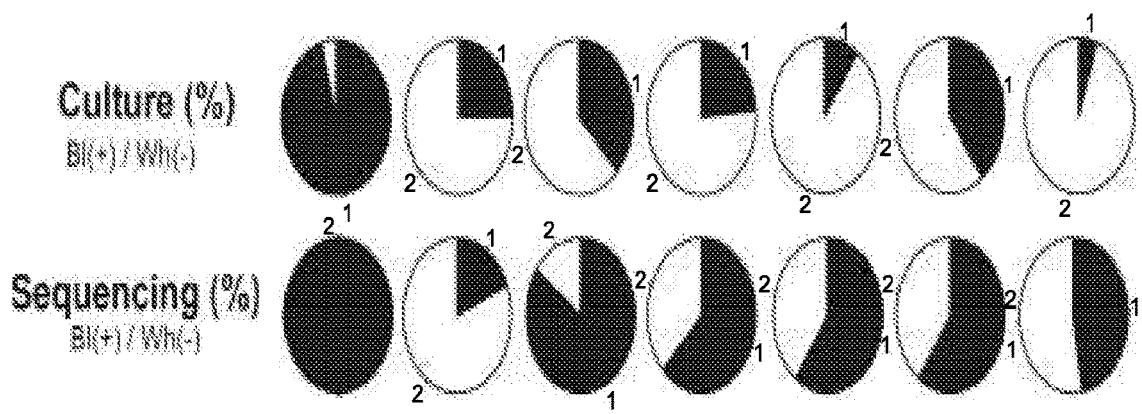
FIGS. 4A-B depict rates of *S. aureus* nasal colonization by sequencing and by culture and *S. aureus* absolute abundance for the seven nasal CSTs. Rate of *S. aureus* nasal colonization varied across nasal CSTs as detected based on sequencing and by culture. In general, sequencing detection revealed higher *S. aureus* prevalence than culturing, except in CST2, where sequencing had lower sensitivity, most likely due to insufficient reads in the context of high total bacterial density (FIG. 4A). As shown by boxplots of *S. aureus* absolute abundance, CST1 and CST6 had the highest *S. aureus* absolute abundance, whereas CST5 had the lowest *S. aureus* absolute abundance (FIG. 4B).
Figure 4B:
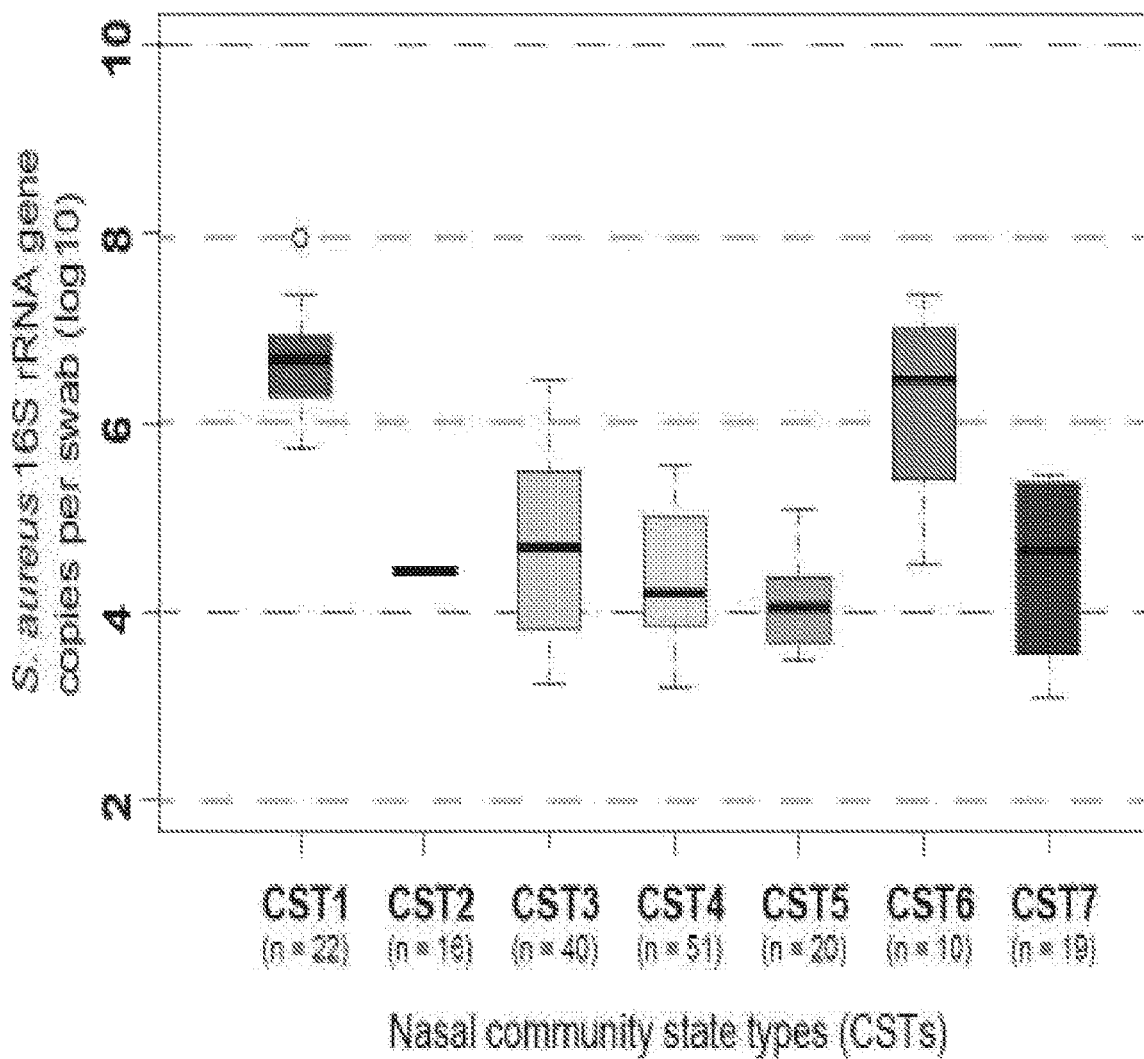

The rates and absolute abundance of *S. aureus* differed among nasal CSTs (FIG. 4A-B). Some taxa predict the presence/absence of *S. aureus*, while others predict *S. aureus* absolute abundance in a threshold-dependent fashion (FIG. 3A). *Dolosigranulum* spp. was the most informative predictor of *S. aureus* presence/absence. Specifically, the rate of *S. aureus* nasal colonization among individuals at or above the *Dolosigranulum* threshold was 16.0% (n=4/25), as compared with 56.0% among the simulated population (n=56/100). Likewise, the investigators observed threshold effects for nasal taxa such as *Propionibacterium granululosum* and *S. epidermidis*; however, *P. granululosum* was negatively correlated with the presence of *S. aureus*, but *S. epidermidis* was positively correlated (*P. granululosum* node n=4/34, 11.8%; *S. epidermidis* node n=13/14, 92.9%) (FIG. 5A).

The *S. aureus* absolute abundance model indicated that having low *Corynebacterium* abundance predicts high *S. aureus* absolute abundance, i.e., Category 5, which comprised $10^6$-$10^7$ *S. aureus* 16S rRNA gene copies per swab (14/28, 50.0%) (FIG. 6A), as compared to the lower Category 5 prevalence in the simulated population (n=16/100, 16.0%) (FIG. 6B). Results from validation tests recapituthat culture-based methods fail to identify a substantial proportion of *S. aureus* carriers, particularly among women, which could serve as unrecognized reservoirs of *S. aureus* (13).

In summary, nasal microbiota is an environmentally derived host phenotype and nasal taxa determine *S. aureus* nasal colonization by influencing *S. aureus* presence/absence and absolute abundance. Nasal microbiota composition is not fixed by host genetics and is therefore susceptible to environmental modification. These findings open the possibility for probiotic strategies to eliminate *S. aureus* nasal colonization. One caveat here is the significant influence of sex and host genetics on nasal bacterial density. In addition, even though early environment had no significant influence in our cohort, which was middle age or older, it could play a role in a younger cohort. In this study, absolute abundance emerged as a critical factor in nasal bacterial interactions and culture-based detection. In particular, the negative interactions between nasal taxa and *S. aureus* depended on absolute abundance thresholds, consistent with the ecological notion that absolute abundances, not relative abundances, reveal the importance of ecological interactions such as competition (16, 17). Thus, the utility of nasal probiotics will rely on whether nasal microbiota composition trumps nasal bacterial density in determining *S. aureus* nasal colonization. Based on the limited influence of host genetics on *S. aureus* nasal colonization (2), we predict that the answer will be "yes".

Laboratory Methods

A. DNA isolation and purification. All samples from each subject were processed in the same batch to control for inter-run variation in lysis and purification. The combined chemical and mechanical lysis was performed as follows: Swab samples were thawed at 4° C. and 100 μl of swab eluent from each sample was transferred to pre-labeled PCT MicroTube (Pressure Bioscience, Inc., South Easton, Mass., USA) containing 50 μl of RLT lysis buffer (Qiagen, Valencia, Calif., USA) and capped with a 150 μl PCT MicroCap (Pressure Bioscience, Inc.). Each capped MicroTube was loaded onto the MicroTube holder and undergo mechanical lysis on the Barocycler NEP 3229 instrument (Pressure Bioscience, Inc.) using the following pressure cycling conditions at 25° C.: increase pressure to 35,000 pounds per square inch (psi) for 15 seconds, then decrease to 14.696 psi for 15 seconds and repeat for 19 more cycles. The lysate was added to 550 μl of RLT lysis buffer and purified using the AllPrep DNA/RNA Mini Kit following manufacturer's instructions. DNA elution was performed with 100 μl of Buffer EB. The purified DNA was used in subsequent qPCR and pyrosequencing analysis.

B. 16S rRNA gene-based broad-coverage qPCR. Each 16S qPCR reaction was performed in 10 μl reaction volumes in PRISM™ 384-well Clear Optical Reaction Plates (Applied Biosystems by Life Technologies, Grand Island, N.Y., USA) using methods as described previously. An in-run standard curve spanning $10^2$-$10^8$ in serial 10-fold dilutions was included in all runs and all samples were analyzed in triplicate reactions. Raw experimental data, including the cycle threshold (Ct) and gene copy number values for each reaction were exported from the Sequence Detection Systems v2.3 software (Applied Biosystems) using a manual Ct threshold of 0.05 and automatic baseline. The Ct standard deviation for each sample was further processed, where samples with Ct standard deviation ≥0.25 were examined for outliers, defined as a single replicate with Ct-value that is ≥0.25 away from the remaining two replicates, which were then removed. The processed data was then used to calculate the finalized Ct-value, as well as the 16S rRNA gene copy number by plotting the Ct-value against linear regression of the in-run standard curve.

C. Generation of 16S rRNA gene V3V6 amplicons. Amplification of the V3V6 region of the 16S rRNA genes in each DNA sample was performed in a 96-well format using 50 μl reactions and thermocycling conditions as previously described. In each optimized 50 μl reaction, 10 μl of DNA was added to 40 μl of PCR reaction mix with a final concentration of 400 nM of each broad range fusion forward primer (5'-CCATCTCATCCCTGCGTGTCTCCGA-CTCAGnnnnnnnn CCTACGGGDGGCWGCA-3' (SEQ ID NO: 1)) and fusion reverse primer (5'-CC-TATCCCCTGTGTGCCTTGGCAGTCTCAGCTGACGA CRRCCRTGCA-3' (SEQ ID NO: 2)), with the underlined portion denoting FLX Lib-L adapter sequence, italicized portion denoting the sample-specific 8-nt barcode sequence, and bolded portion denoting 16S rRNA gene primer sequence, 10×PCR buffer without MgCl$_2$ (Invitrogen), 2.5 mM MgCl$_2$, 0.5 mM dNTP mix, 0.067 U/μl Platinum® Taq DNA Polymerase (Invitrogen), and molecular grade H$_2$O using the following thermocycling condition: 90 seconds at 95° C. for initial denaturation and UNG inactivation, 30 seconds at 95° C. for denaturation, 30 seconds at 62° C. for annealing, 30 seconds at 72° C. for extension, with the annealing temperature decreasing by 0.3° C. for each subsequent cycle for 19 cycles, followed by 10 cycles of amplification consisting of 30 seconds at 95° C. for denaturation, 30 seconds at 45° C. for annealing, 30 seconds at 72° C. for extension, and a final extension for 7 minutes at 72° C. and cool down to 15° C. PCR products were frozen immediately at −20° C. until further processing. In each fusion PCR experiment, negative and positive extraction controls were included, as well as PCR controls including a no-template control, a positive bacterial control (*E. coli* genomic DNA at 1 pg/μl), and a human DNA control (human genomic DNA at 10 ng/μl). The resultant fusion PCR product were analyzed using 1% E-Gel® 96 Agarose (Invitrogen) to confirm PCR amplification and product band size. The barcoded 16S rRNA gene amplicons from each sample underwent 4 ten-fold dilutions and were quantified using the 16S rRNA gene-based broad-coverage qPCR described earlier. The resultant barcoded amplicons were pooled in an equimolar fashion. The pooled barcoded 16S rRNA gene amplicon library underwent emulsion PCR, bead enrichment and recovery, and pyrosequencing analysis on the Genome Sequencer FLX instrument (454 Life Sciences, Branford, Conn., USA).

Bioinformatics Methodological Details

A. Chimeric sequence removal. The investigators first converted the standard flowgram format (SFF) files into fasta sequence and quality files using a combination of in-house Perl-based wrappers and the 454 Sequencing System Software 1. Next, the investigators identified chimeric sequences de novo using U-Search's cluster utility (U-Search version 5.0•144) and U-Chime at the 99% threshold. Only non-chimeric sequences were included in subsequent analysis.

B. Sequence barcode removal, binning, and quality filtering. The investigators next assigned each pyrosequence to its original sample and scanned for primer sequence using a QIIME utility. Pyrosequences without valid barcode or primer were excluded. The investigators filtered the demultiplexed pyrosequences based on: a) length (150 bp-920 bp), b) number of degenerate bases (a maximum of six), c) mean quality score (a lower threshold of 25), and d) homopolymer length (a maximum consecutive run of six). Lastly, the investigators trimmed each sequence based on quality using a sliding window of 50 bp and a quality score threshold of 25.

C. Taxonomic Classification. The resultant demultiplexed and quality-checked 16S rRNA gene sequences were classified at each taxonomic level (i.e., phylum, class, order, family, genus) at ≥80% bootstrap confidence level using a web service for the Naïve Bayesian Classifier (RDP Release 10, Update 28). Sequences classified at <80% bootstrap confidence level are reported with the assigned taxon and a "Cl<0.80" notation. The taxonomic classifications assigned to the sequences through the RDP Classifier fall into the modern high-order bacterial proposed by Garrity et. al. A total of 327,716 bacterial 16S rRNA gene sequences were obtained and classified. Classification results for each sample are enumerated to generate an abundance-based matrix for data analysis. Bacterial taxa that comprised 0.2% of total sequences were included in subsequent analysis.

D. Species classifier development and validation. The Naïve-Bayesian RDP Classifier is one of the current gold standards for high-throughput classification of bacteria 16S rRNA gene sequences; however, at this time, it does not provide species level classification, which limits our ability to examine *Staphylococcus* and of other nasal taxa at the species-level, if sufficient resolution exists. In order to achieve this, we re-built the RDP Classifier with an external taxonomy and curated sequences, with the particular goal of improving *Staphylococcus* species resolution because it is of major ecological importance in the nasal cavity.

Thus, the investigators developed a pipeline that will read an external taxonomy, create a database to maintain the taxonomic information, build training files from the database solution, re-train the RDP Classifier, and generate classifications for a set of query sequences. The general workflow is depicted below:

D1. Training set curation. Fundamental to the entire process mentioned above is the acquisition of a training set, which can be used as a model for generating taxonomic classifications. *Staphylococcus* sequences that are missing or underrepresented in our training set may be assigned incorrectly or with low confidence level. Greengenes and RDP *Staphylococcus* sequences were used as the core of our training set and curation is ongoing.

D1a. Greengenes. The majority of the training set is comprised of sequences from the Greengenes taxonomy. While trying to build raw training files (described in the section titled "Creating Raw Training Files"), it became apparent that polyphyletic groups exist in the current Greengenes taxonomy. Re-training the RDP Classifier was not possible until these groups were either resolved, or removed from the taxonomy. The approach to overcoming this obstacle was to insert the polyphyletic taxonomy into a database, and then build training files from the database solution such that a given sequence's membership in a polyphyletic group is clearly indicated.

A taxon is considered polyphyletic if it has more than one parent. Consider the two lineage strings below:
182310
Root;k_Bacteria;p_Proteobacteria;c_Gammaproteobacteria; o_Alteromonadales;f_Alteromonadaceae;g_Alteromonas: s_Alteromonasmarina
250345
Root;k_Bacteria;p_Proteobacteria;c_Gammaproteobacteria: o_Oceanospirillales;f_Alteromonadaceae;g_Marinobacter: s_

The family Alteromonadaceae is polyphyletic because it has two parents. Our solution generates training files that indicate this relationship in the manner demonstrated below:
182310
Root; k_Bacteria; p_Proteobacteria;c_Gammaproteobacteria;o_KNOWN_POLYPHYLETIC_GROUP[Alteromonadales, Oceanospirillales];f_Alteromonadaceae;

D1b. Ribosomal Database Project. A set of training sequences was also acquired from the RDP project. This set is comprised of solely of type strains assigned to the genus *Staphylococcus* to increase the confidence of species-level assignment. The RDP sequence set underwent chimera check using UCHIME.

D2. Database Design. To facilitate efficient maintenance of and access to the taxonomy, a relational database solution was implemented. In order to optimize efficient querying of the database, reduce space consumption, and to eliminate redundant entries within the database, a table for each rank was implemented; the consequence of this is that it is only necessary to insert a specific taxon once. Synonym tables were added to facilitate querying of the database in a manner that allowed membership in a polyphyletic group to be reflected in the resulting training files. The database design is provided in the diagram attached with this document:

To insert sequences into the database, the insert_taxonomy.py is utilized:

```
python insert_taxonomy.py
-t taxonomy_file.txt
-o parsed_taxonomy_file.txt
-s RDP
-b yes
-a localhost
-m 16S_TAXONOMY_RDP_STAPH
-u root
-p password
-c create_all_tables.sql
  -f seqs.fasta
```

Argument Explanation:
* -t The taxonomy file containing all the lineage strings
* -o The name of the parsed taxonomy file that will be generated
* -s Source of the taxonomy
* -b Flag to indicate whether a new database build is to be used (values of y or yes will indicate to do so)
* -a Database host
* -m Database name
* -u Username
* -p Password
* -c Optional argument indicating the script for creating the database tables
* -t Optional argument indicating the taxonomy dictionary that will be used as a schema to build the database from
* -f The fasta file containing the sequences in the taxonomy D3. Creating Training Files. The build_taxonomy.py script is used to generate training files from the database. Usage is as follows:

```
python/PATH/build_taxonomy.py
-t yes
-o/PATH/training_rdp_download_1258seqs.txt
-a localhost
-d 16S_TAXONOMY_RDP_STAPH
-u root
-p password
```

Argument Explanation:
* -t Optional argument that indicates whether or not a training file is to be generated. Any value will indicate yes.
* -o Output file
* -s Optional argument that indicates the source of the taxonomy. This is only used if an original taxonomy file is to be generated.
* -a Hostname
* -d Database name
* -u Username
* -p Password The RDP Classifier training requires two raw training files as inputs: a taxonomy tree file containing the hierarchical taxonomy information, and a sequence file with lineage strings included in the headers. Both of these files are created with the create_raw_training_files.py script, which performs the following steps: 1. Modify/parse the taxonomy, 2. Modify/parse the sequence file, 3. Create the raw taxonomy tree file, and 4. Generate the updated sequence file. In order to run this script, the following command must be executed:

```
python create_raw_training_files.py
<taxonomy_file>
<sequence_file>
<output_raw_taxonomy_file>
<output_raw_seq_file>
```

Argument Explanation:
* <taxonomy_file>—The file generated by build_taxonomy.py containing sequence ids and associated lineage strings
* <sequence_file>—The fasta file generated by build_taxonomy.py containing all the training sequences
* <output_raw_taxonomy_file>—Output file containing hierarchical taxonomy tree
* <output_raw_seq_file>—Output sequence file with lineage included in the headers D4. Modifying the Taxonomy. A hierarchical taxonomy tree file will be generated as the output; however, for the tree to be valid, certain modifications to the taxonomy must be made. It is a strict requirement that all sequences in the taxonomy must not only have names for all ranks, but they must also all be classified down to the same level. Consider the sequence 152262, which has a lineage of:
  k_Bacteria;p_Chlamydiae;c_Chlamydiae;o_Chlamydiales;f_;g_
Our script will parse this lineage string such that the following, valid string is generated:
  k_Bacteria;p_Chlamydiae;c_Chlamydiae;o_Chlamydiales;f_Bacteria.Chlamydiae.Chlamydiae.Chlamydiales.unclassified_family;
  g_Bacteria.Chlamydiae.Chlamydiae.Chlamydiales.Bacteria.Chlamydiae.Chlamydiae.Chlamydiales.unclassified_family.unclassified_genus;
  s_Bacteria.Chlamydiae.Chlamydiae.Chlamydiales.Bacteria.Chlamydiae.Chlamydiae.Chlamydiales.unclassified_family.Bacteria.Chlamydiae.Chlamydiae.Chlamydiales.Bacteria.Chlamydiae.Chlamydiae.Chlamydiales.unclassified_family.unclassified_genus.unclassified_species D5. Modifying the Sequence File. All sequences in the representative sequence file are modified such that they are in the format:
  domain;phylum;class;order;family;genus;species D6. The Taxonomy Tree File
create_raw_training_files.py modifies the taxonomy, and then generates the hierarchical taxonomy tree file from the revised taxonomy. The format for the taxonomy tree is depicted below:
  taxid*taxon name*parent taxid*depth*rank
  taxid, the parent taxid, and depth should be in integer format. depth indicates the depth from the root taxon. An example tree is given below:
  1*Bacteria*0*0*domain
  765*Firmicutes*1*1*phylum
  766*Clostridia*765*2*class
  767*Clostridiales*766*3*order
  768*Clostridiaceae*767*4*family
  769Clostridium768*5*genus
  160*Proteobacteria*1*1*phylum
  433*Gammaproteobacteria*160*2*class
  586*Vibrionales*433*3*order
  587*Vibrionaceae*586*4*family
  588Vibrio587*5*genus
  592Photobacterium587*5*genus
  552*Pseudomonadales*433*3*order
  553*Pseudomonadaceae*552*4*family
  554Pseudomonas553*5*genus
  604*Enterobacteriales*433*3*order
  605*Enterobacteriaceae*604*4*family
  617Enterobacter605*5*genus
  161*Alphaproteobacteria*160*2*class
  260*Rhizobiales*161*3*order
  261*Rhizobiaceae*260*4*family
  262Rhizobium261*5*genus D7. Re-training the RDP Classifier. To re-train the classifier, it is necessary to create parsed training files from the raw training data. Assuming the two raw files are created in mydir/mydata: mytaxon.txt and mytrainseq.fasta, the user will need to run the command to create parsed training files:
  mkdir/PATH/mydata/mydata_trained
    java -Xmx1g
      -cp/PATH/rdp_classifier-version.jar edu.msu.cme.rdp.classifier.train.ClassifierTraineeMaker
  /PATH/mydata/mytaxon.txt
  /PATH/mydata/mytrainseq.fasta
  1
  version1
  test
  /PATH/mydata/mydata_trained Argument Explanation:
* <mydata/mytaxon.txt> Contains the hierarchical taxonomy information
* <mydata/mytrainseq.fasta> Contains the raw training sequences
* <1> The trainset_no to mark the training files generated
* <version1> Holds the modification information of the taxonomy
* <mydata_trained> Specifies the output directory Four parsed training files will be created and saved into directory mydata_trained:
* bergeyTrainingTree.xml
* genus_wordConditionalProbList.txt
* logWordPrior.txt
* wordConditionalProbIndexArr.txt After this is accomplished, the rRNAClassifier.properties file (found with the RDP source code) needs to be copied into the directory containing the files mentioned above. Effectively, these files will serve as the model from which classifications will be generated.

D8. Generating Classifications. To classify sequences, the user can either choose to execute the RDP Classifier source code by itself, or to use the species_classification_generator.py script. To execute the RDP Source Code, the user will need to execute the following command:
  java -Xmx1g -jar/PATH/rdp_classifier-version.jar
    -t/PATH/mydata/rRNAClassifier.properties
    -q/PATH/sampledata/testQuerySeq.fasta
    -o/PATH/testquery.out Argument Explanation:
* -jar The RDP jar file to use
* -t The rRNAClassifier.properties file
* -q Query sequence file
* -o Output file NOTE: If the -t option is not used, the classifier will use the standard training set, and species-level classifications will not be generated. The species_classification_generator.py script does more than just produce the classifications. It parses headers of the .fna files produced by our current version of the pyro sequencing pipeline, runs the RDP Classifier on the sequences contained in the .fna files, parses the output, upload the classification results into a database, and generates the .xls files. To run this script the user will need to execute the following command:
  python species_classification_generatorpy
    -d seqs/
    -r 090712_omoss_test
    -s localhost
    -m PYRO_SEQ_CLASSIFICATIONS
    -u root
    -p password -j/PATH/rdp_classifier-2.4.jar
-c/PATH/ClassificationReporter.jar
-t/PATH/rRNAClassifierproperties
Argument Explanation:
* -d Data directory containing the sequences to be classified
* -r The name of the run that will be used to identify the database tables containing the results of the classification
* -s MySQL hostname
* -m MySQL database to hold classifications
* -u MySQL username
* -p User password
* -j Path to the RDP Classifier jar file
* -c Path to the ClassificationReporter.jar file
* -t Path to the rRNAClassifierproperties file D10. Testing the Re-trained Classifier. To assess the accuracy of the re-trained RDP classifier, multiple controlled tests were performed using 16S rRNA gene sequences from the training set and from Genbank.

D10a. Initial Testing. All sequences from *Staphylococcus epidermidis* and *Staphylococcus aureus* from the training set were compiled into two groups. Each set of sequences was classified using the re-trained classifier. Initial statistical analyses indicated that 23% of the *S. aureus*, and 50% of the *S. epidermidis* sequences were assigned incorrectly at the species level using full set.

| Species | Correctly assigned Sequences | Input Sequences |
|---|---|---|
| S. aureus | 281 (76.8%) | 366 |
| S. epidermidis | 116 (49.8%) | 233 |

D10b. Optimizing the *Staphylococcus* training set. To assess whether the misclassifications could be attributed to erroneous designations in the training taxonomy, the RDP training set was checked by first clustering the sequences at 97% threshold using UCLUST and the highest quality sequence from each cluster was checked against the Genbank 16S rRNA sequence database (Bacteria and Archaea) by BLAST. The top hit was identified and compared to the original RDP assignment. Sequences with non-matching taxonomic assignments were removed from the training set and the classifier was re-trained. Further testing revealed that this significantly improved the classification; now, 96.1% of *S aureus* and 89.5% of *S. epidermidis* sequences are accurately classified to the species-level.

| Species | Correctly assigned Sequences | Input Sequences |
|---|---|---|
| S. aureus | 274 (96.1%) | 285 |
| S. epidermidis | 86 (89.5%) | 96 |

E. Additional analysis of *Staphylococcus* sequences. For sequences that were assigned to *Staphylococcus* but had species assignment at <0.80 confidence level, the investigators dereplicated the sequences at 97% similarity threshold using UCHIME, then manually extracted representative sequences of each cluster from the dereplication, verified if they were *S. aureus* using BLAST. This showed that sequences assigned to *S. aureus* <0.80 and *S. auricularis* <0.80 were *S. aureus*, which we included as *S. aureus* sequences in subsequent analysis.

Nasal Microbiome Analyses
Definitions and Metrics

Nasal community state type (i.e., nasal CST): The major nasal microbiota profiles, as identified by hierarchal clustering.

Nasal bacterial density: The amount of nasal bacteria present in an individual's nasal cavity, which in this study was estimated based on the total number of 16S rRNA gene copies detected per swab.

Prevalence: The proportion of study population found to have a variable of interest, such as a particular nasal CST or nasal bacterial taxon.

Proportional abundance: Proportion of an individual's nasal microbiota comprised a specific nasal bacterial taxon. Using the taxonomically-classified sequence data, we calculated the proportional abundance for each nasal bacterial taxon as: (Number of sequences assigned to the taxon from the sample)/(Total number of sequences from the sample).

Absolute abundance: The counts of a specific nasal bacterial taxon comprising an individual's nasal microbiota. We combined proportional abundance with nasal bacterial density to calculate taxon absolute abundance as: (Proportional abundance of the taxon from the sample)×(nasal bacterial density of the sample).

Nasal microbiota composition: An individual's nasal microbiota characterized by the nasal bacterial taxa present, reported in either proportional abundance or absolute abundance.

Presence/absence of *S. aureus* by sequencing: Detection of $>=2$ sequences assigned to *S. aureus* is categorized as presence of *S. aureus* by sequencing, whereas singletons or no *S. aureus* sequences are categorized as absence. Detection of *S. aureus* by sequencing is affected by high total nasal bacterial density. *S. aureus* sequences may also be assigned incorrectly by our custom RDP species-level classifier if the *S. aureus* sequence type is missing or underrepresented in our training set.

*Staphylococcus aureus* absolute abundance: Absolute abundance of *S. aureus* is calculated as the product of nasal bacterial density and proportional abundance of *S. aureus*. The assessment of *S. aureus* by sequencing is affected by high total nasal bacterial density. *S. aureus* sequences may also be assigned incorrectly by our custom RDP species-level classifier if the *S. aureus* sequence type is missing or underrepresented in our training set.

Ecological Analyses

1. Characterization of nasal bacterial density. We reported the range, median, and inter-quartile range of participants' nasal bacterial density, calculated using R (version 3.0.1). Boxplots of nasal bacterial density for each nasal CST was also generated using R.

2. Assignment of nasal community state types. To identify community state types (CSTs), the investigators used proportional abundance data (Euclidean distance) in hierarchal clustering by Ward linkage using cutree through an iterative process as previously described. Comparisons of the 6-, 7-, and 8-CST solutions revealed that seven-CST solution to be the most parsimonious and effective. Heatmap visualization was then generated using nasal microbiota composition (in proportional abundance) from each participant, grouped by nasal CST assignment (FIG. 1B).

3. Identification of indicator taxa for nasal community state types. We identified the nasal bacterial taxa uniquely associated with each nasal CST using indicator analysis from the labdsv package (R package version 1.6-1). The indicator species analysis is an objective assessment of a particular taxon's representation of an environment or a study group. A taxon's indicator value (IV) for a study group is determined based on its proportional abundance and prevalence in the given study group. The IV ranges from 0 to 1, with 0 as no indication to 1 as perfect indication. To test the null hypothesis of no difference between our observation and what can be observed by chance, IV null distributions were built by Monte Carlo procedure using 1,000 resampled datasets with randomized study group assignments. The P-value for each observed IV was determined based on its location within the null distribution and adjusted for false-discovery. A significance level of P=0.10 was used and results are shown in Table 2.

4. Association between host genetics and nasal microbiota composition. The investigators assessed the correlation between nasal microbiota composition and host genetics based on nasal CST concordance in twin pairs and difference in pairwise ecological distance between twin types. The investigators calculated the nasal CST concordance for monozygotic and dizygotic twin pairs, where a twin pair having identical nasal CST assignments marks concordance. The investigators computed the pairwise ecological distance among all study participants based on the nasal microbiota composition (proportional abundance) in three distance metrics: Jaccard's, Bray-Curtis, and Euclidean. Using a bootstrap-based approach, the investigators calculated the difference in pairwise distance in three experiments of 1,000 iterations: a) PairwiseDist$_{MZ\ (Male\ or\ Female)}$-PairwiseDist$_{DZ\ (Any\ Sex)}$, b) PairwiseDist$_{MZ\ (Male\ or\ Female)}$-PairwiseDist$_{DZ\ (Same\ Sex)}$, and C) PairwiseDist$_{MZ\ (Male\ or\ Female)}$-PairwiseDist$_{Random\ pair\ (Same\ Sex)}$. The correlation in twin pairs would be considered statistically significant if the bootstrapped 95% confidence interval of the difference in pairwise distance does not cross zero. Results are shown in Table 4.

5. Visualization of nasal microbiota composition by nasal CST and for each twin type. We also visualized the overall nasal microbiota composition by nasal CST (FIG. 1C) and for each twin type (FIGS. 2A-C) using proportional abundance data in Euclidean distance by non-metric multidimensional scaling (nMDS), which is a non-parametric ordination technique to reduce a highly multidimensional community composition data into a two-dimensional ordination plot. The nMDS ordination and visualization were generated using the vegan package (R package version 1.17-8).

6. Association between host genetics and of nasal bacterial density. The investigators assessed the correlation between nasal bacterial density and host genetics using intra-class correlation coefficient (ICC) in R. The investigators determined correlation of nasal bacterial density ($\log_{10}$) for monozygotic twin pairs and dizygotic twin pairs based on sex- and age-adjusted ICC. The resultant ICC represents the fraction of total variance that is due to variation between groups, calculated using the pooled mean and standard deviation; consequently, the larger the ICC, the smaller the within-twin variation, and vice versa. The correlation in twin pairs was statistically significant if the 95% confidence interval of the ICC does not cross zero.

7. Heritability of nasal bacterial density. A standard biometrical heritability analysis was performed for nasal bacterial density in $\log_{10}$ to estimate the relative contribution of genetic and environmental factors. The twin study leverages the fact that monozygotic (MZ) twins share all their genes, whereas dizygotic (DZ) twins share approximately 50% of their genes as other types of siblings. As such, biometrical heritability analysis separates total phenotype variance (V) into four variance compartments: V=A+D+C+E, where A refers to additive genetic effects, D refers to genetics effects due to dominance, C refers to shared environmental effects, and E refers to non-shared environmental effects.

The investigators could not simultaneously estimate the effects of D and C because they are confounded. Therefore, the investigators fitted separate ACE and ADE models. The investigators also fitted sub-models AE, DE, CE, and E, as the simpler models may sufficiently explain the data. The investigators chose the non-nested model with the lowest Akike's Information Criteria (AIC), and the investigators selected the most parsimonious nested model with $\chi^2$ likelihood ratio p>0.05. All analyses were performed using the statistical package R (version 3.0.2) and the R package mets: Analysis of Multivariate Event Times (version 0.2.6).

After testing the assumptions of equal regression, intercept, and residual variance for twin 1 and twin 2 as well as for MZ and DZ twins, the investigators found that the ADE model had the lowest AIC and that it could be further reduced to a AE model because of its lower log likelihood ratio; however, the AE model could not be reduced to an E model (Table 3). Taken together, these results showed both heritability and non-shared environmental influences on nasal bacterial density, with a smaller heritability effect (29.8%, 95% CI: 6%-54%) and a larger non-shared environmental effect (70.1%, 95% CI: 46%-94%).

Of note, the final and intermediate models, as shown in Table 5 included adjustment for sex and age. While age was not associated with nasal bacterial density and its inclusion had no significant impact on modeling outcome, sex emerged as a significant factor as reported in the main text.

8. Association between nasal bacterial density and host factors including sex. The median and quantile of nasal bacterial density by sex, history of atopic disease and psoriasis, and by current smoking status were calculated using R. We also plotted the nasal bacterial density ($\log_{10}$) as scattered plots with median (FIG. 5A). Difference in nasal bacterial density based on each host factor was compared using two non-parametric tests: the Wilcoxon-ranked sum and Kolmogorov-Smirnov test, with a significance level of $\alpha$=0.05, with results as shown in Table S5.

To determine if the significant sex difference in nasal bacterial density could be explained by CST prevalence, the nasal CST prevalence for men versus women is as shown in Table 3, which we compared by $\chi^2$ test. The investigators further assessed if men and women have significantly different nasal bacterial density, irrespective of nasal CST using quasi-Poisson model comparing the outcome of nasal bacterial density, stratified by the seven nasal CSTs. Women with CST3 was used as the reference and the results are shown in Table S6, which showed that men and women had significantly different nasal bacterial density even after adjusting for nasal CST.

9. Association of nasal bacterial density with microbiota composition: The investigators compared the nasal bacterial density across CSTs by analysis of variance (ANOVA) in R and reported the median nasal bacterial density and interquartile range for each nasal CST in Table 3. The significant difference in sex-adjusted nasal bacterial density across nasal CSTs can also be seen in Table 7.

10. Decision tree analysis: Using decision tree analysis with recursive partitioning and splitting by information criteria using the rpart package, a derivation model was built used a simulated population of 100 randomly-drawn (without replacement) individuals. Using the derivation set, two outcomes were determined: *S. aureus* presence/absence and *S. aureus* absolute abundance ($\log_{10}$) in five categories (Category 1-5). Among the nasal bacterial taxa detected, those significantly associated with *S. aureus* nasal colonization were incorporated in the derivation model, which included taxa with conflicting associations in earlier studies. The derivation decision tree model incorporated the absolute abundances ($\log_{10}$) of the following nasal taxa: *Anaerococcus*, *Finegoldia*, *Peptoniphilus*, *Dolosigranulum*, *Corynebacterium*, Unclassified Corynebacteriaceae, *Propionibacterium acnes*, *Propionibacterium granulosum*, *Simonsiella* <0.80, *Staphylococcus epidermidis* (including <0.80), and *Moraxella*.

A model was derived for each outcome of interest and the branches were trimmed down to include only those with 10 or more individuals in each terminal node (except for *Simonsiella*<0.80, which was an early $2^{nd}$ node). A predicted outcome was assigned to each terminal node (i.e., as predicting either *S. aureus* presence or absence or as predicting a *S. aureus* absolute abundance category) (FIGS. 5A and 6A).

Validation test for the predicative thresholds was conducted using 10 additional simulated populations of 100 randomly-drawn (without replacement) individuals. The validation results were determined to support the initial model if the predicative thresholds produced results that are more similar to the predicted outcome than the underlying simulated population (FIGS. 5B and 6B-C).

11. Correlation between *S. aureus* absolute abundance and culture outcome. The investigators calculated *S. aureus* absolute abundance among non-CST1 individuals with *S. aureus* detectable by DNA sequencing. The investigators divided these individuals into four categories based on ten-fold differences in *S. aureus* absolute abundance (<$10^4$, $10^4$-<$10^5$, $10^5$-<$10^6$, $10^6$-$10^7$). We plotted the histograms of each *S. aureus* absolute abundance category in men and women (FIG. 5B), which showed that women most often fell into to two lowest absolute abundance categories (<$10^4$ and $10^4$-<$10^5$) while men were more likely to have the middle two categories ($10^4$-<$10^5$ and $10^5$-<$10^6$). The correlation between *S. aureus* nasal culture and *S. aureus* absolute abundance category was shown in FIG. 6C. The relationship between *S. aureus* nasal culture (outcome) to other variables including *S. aureus* absolute abundance category, sex, history of atopic disease and psoriasis, and current smoking status was assessed using a multivariate linear regression model, which showed that sex was not a significant predictor of *S. aureus* culture outcome (P=0.79), after adjusting for *S. aureus* absolute abundance category (P<0.001), where the model indicated that with each ten-fold increase in *S. aureus* absolute abundance, the probability of having a positive *S. aureus* culture increases by 30.4% (F-statistic 7.19 on 68 degrees of freedom, Model P<0.001).

TABLE 6

|  | Median | Inter-Quartile Range | | Wilcoxon p-value | Kolmogorov-Smirnov p-value |
|---|---|---|---|---|---|
|  |  | 25th | 75th |  |  |
| Overall |  | 4.07E+06 | 7.08E+06 | n/a | n/a |
| Sex |  |  |  |  |  |
| Women (n = 102) | 2.97E+06 | 1.33E+06 | 9.11E+06 |  |  |
| Men (n = 76) | 7.94E+06 | 2.20E+06 | 4.30E+07 |  |  |
| Difference |  |  |  | p < 0.001 | p = 0.005 |
| History of atopic diseases |  |  |  |  |  |
| Yes (n = 54) | 4.46E+06 | 1.90E+06 | 1.50E+07 |  |  |
| No (n = 124) | 4.39E+06 | 1.50E+06 | 1.80E+07 |  |  |
| Difference |  |  |  | p = 0.47 | p = 0.35 |
| History of psoriasis |  |  |  |  |  |
| Yes (n = 15) | 6.41E+06 | 4.80E+06 | 2.10E+07 |  |  |
| No (n = 158) | 3.69E+06 | 1.57E+06 | 1.63E+07 |  |  |
| Difference |  |  |  | p = 0.22 | p = 0.12 |
| Current smoker |  |  |  |  |  |
| Yes (n = 33) | 3.23E+06 | 1.66E+06 | 9.59E+06 |  |  |
| No (n = 145) | 4.44E+06 | 1.59E+06 | 1.96E+07 |  |  |
| Difference |  |  |  | p = 0.61 | p = 0.53 |

TABLE 7

|  | Men*** | Women*** |
|---|---|---|
| CST1** (*S. aureus*) | 1.20E+07 | 4.68E+06 |
| CST2*** (*Enterobacteriaceae*) | 8.72E+07 | 3.04E+07 |
| CST3*** (*S. epidermidis*) | 4.95E+06 | 2.03E+06 (Reference) |
| CST4*** (*Propionibacterium*) | 2.26E+07 | 8.51E+06 |
| CST5 (*Corynebacterium*) | 9.30E+06 | 3.68E+06 |
| CST6* (*Moraxella*) | 1.58E+07 | 6.09E+06 |
| CST7 (*Dolosigranulum*) | 9.87E+06 | 3.90E+06 |

REFERENCES

1. A. van Belkum et al., Reclassification of *Staphylococcus aureus* nasal carriage types. *The J Infect Dis* 199, 1820-1826 (2009).

2. P. S. Andersen et al., Influence of host genetics and environment on nasal carriage of *Staphylococcus aureus* in danish middle-aged and elderly twins. *J Infect Dis* 206, 1178-1184 (2012).

3. M. Li et al., Symbiotic gut microbes modulate human metabolic phenotypes. *Proc Natl Acad Sci USA* 105, 2117-2122 (2008).

4. J. Peterson et al., The NIH Human Microbiome Project. *Genome Res* 19, 2317-2323 (2009).
5. E. A. Grice et al., Topographical and temporal diversity of the human skin microbiome. *Science* 324, 1190-1192 (2009).
6. K. P. Lemon et al., Comparative analyses of the bacterial microbiota of the human nostril and oropharynx. *mBio* 1, (2010).
7. D. N. Frank et al., The human nasal microbiota and *Staphylococcus aureus* carriage. *PLoS One* 5, e10598 (2010).
8. Y. Uehara et al., Bacterial interference among nasal inhabitants: eradication of *Staphylococcus aureus* from nasal cavities by artificial implantation of *Corynebacterium* sp. *J Hosp Infect* 44, 127-133 (2000).
9. M. Yan et al., Nasal microenvironments and interspecific interactions influence nasal microbiota complexity and *S. aureus* carriage. *Cell Host Microbe* 14, 631-640 (2013).
10. A. Camarinha-Silva, R. Jauregui, D. H. Pieper, M. L. Wos-Oxley, The temporal dynamics of bacterial communities across human anterior nares. *Environ Microbiol Rep* 4, 126-132 (2012).
11. C. M. Liu et al., BactQuant: an enhanced broad-coverage bacterial quantitative real-time PCR assay. *BMC microbiology* 12, 56 (2012).
12. C. M. Liu et al., Male circumcision significantly reduces prevalence and load of genital anaerobic bacteria. *mBio* 4, e00076 (2013).
13. H. F. Wertheim et al., The role of nasal carriage in *Staphylococcus aureu* infections. *Lancet Infect Dis* 5, 751-762 (2005).
14. W. J. Munckhof et al., Nasal carriage of *Staphylococcus aureu*, including community-associated methicillin-resistant strains, in Queensland adults. *Clin Microbiol Infect* 15, 149-155 (2009).
15. K. Olsen et al., *Staphylococcus aureus* nasal carriage is associated with serum 25-hydroxyvitamin D levels, gender and smoking status. The Tromso Staph and Skin Study. *Eur J Clin Microbiol Infect Dis* 31, 465-473 (2012).
16. G. F. Gause, *The struggle for existence*. (The Williams & Wilkins company, Baltimore, 1934).
17. N. Fierer et al., From Animalcules to an Ecosystem: Application of Ecological Concepts to the Human Microbiome. *Annu Rev Ecol Evol Syst* 43, 137-155 (2012).

What is claimed is:

1. A method of treating *Staphylococcus aureus* nasal colonization, the method comprising the steps of:
    collecting a nasal swab sample from a subject;
    extracting nucleic acid from the nasal swab sample;
    sequencing the extracted nucleic acid to generate sequence data;
    analyzing the sequence data to determine an abundance of *Dolosigranulum* species represented as rRNA gene copies in the nasal swab sample;
    determining that the abundance of *Dolosigranulum* rRNA is below a threshold level of $1.2 \times 10^6$ gene copies in the nasal swab sample collected from the subject;
    identifying the subject as requiring treatment for *Staphylococcus aureus* nasal colonization based on the abundance of *Dolosigranulum* rRNA being below the threshold level; and
    administering a pharmaceutical composition to the subject to treat the *Staphylococcus aureus* nasal colonization, wherein the pharmaceutical composition comprises a therapeutically effective amount of at least one probiotic organism, and the at least one probiotic organism comprises *Dolosigranulum* species.

2. The method of claim 1, wherein at least a portion of the *Staphylococcus aureus* is resistant to methicillin.

3. The method of claim 1, further comprising administering at least one antibiotic to the subject.

4. The method of claim 3, wherein the at least one antibiotic comprises mupirocin.

5. The method of claim 1, wherein the pharmaceutical composition comprises at least one pharmaceutically acceptable carrier.

6. The method of claim 5, wherein the at least one pharmaceutically acceptable carrier comprises a growth medium to sustain the at least one probiotic organism prior to administration to the subject.

7. The method of claim 1, wherein the pharmaceutical composition is intranasally administered to the subject.

8. The method of claim 1, wherein the *Dolosigranulum* species is *Dolosigranulum pigrum*.

9. The method of claim 1, wherein the pharmaceutical composition further comprises a therapeutically effective amount of a *Corynebacterium* species.

10. The method of claim 9, wherein the *Corynebacterium* species is *Corynebacterium pseudodiphtheriticum*.

11. A method of treating *Staphylococcus aureus* nasal colonization, the method comprising the step of:
    administering a pharmaceutical composition to a subject in need of treatment for *Staphylococcus aureus* nasal colonization, wherein the subject exhibits an abundance of *Dolosigranulum* rRNA below a threshold level of $1.2 \times 10^6$ 16S rRNA gene copies in a nasal swab sample of the subject, and wherein the pharmaceutical composition comprises a therapeutically effective amount of at least one probiotic organism, and the at least one probiotic organism comprises *Dolosigranulum* species, thereby treating the *Staphylococcus aureus* nasal colonization.

12. The method of claim 11, wherein at least a portion of the *Staphylococcus aureus* is resistant to methicillin.

13. The method of claim 11, further comprising administering at least one antibiotic to the subject.

14. The method of claim 13, wherein the at least one antibiotic comprises mupirocin.

15. The method of claim 11, wherein the pharmaceutical composition comprises at least one pharmaceutically acceptable carrier.

16. The method of claim 15, wherein the at least one pharmaceutically acceptable carrier comprises a growth medium to sustain the at least one probiotic organism prior to administration to the subject.

17. The method of claim 11, wherein the pharmaceutical composition is intranasally administered to the subject.

18. The method of claim 11, wherein the *Dolosigranulum* species is *Dolosigranulum pigrum*.

19. The method of claim 11, wherein the pharmaceutical composition further comprises a therapeutically effective amount of a *Corynebacterium* species.

20. The method of claim 19, wherein the *Corynebacterium* species is *Corynebacterium pseudodiphtheriticum*.

* * * * *